United States Patent
Coon et al.

(10) Patent No.: US 10,247,711 B2
(45) Date of Patent: Apr. 2, 2019

(54) QUALITY CONTROL REAGENTS AND METHODS

(71) Applicant: Promega Corporation, Madison, WI (US)

(72) Inventors: Joshua Jacques Coon, Middleton, WI (US); Michael M. Rosenblatt, Middleton, WI (US); Marjeta Urh, Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 14/180,125

(22) Filed: Feb. 13, 2014

(65) Prior Publication Data

US 2014/0230517 A1 Aug. 21, 2014

Related U.S. Application Data

(60) Provisional application No. 61/764,312, filed on Feb. 13, 2013.

(51) Int. Cl.
*G01N 30/72* (2006.01)
*G01N 30/86* (2006.01)
G01N 30/02 (2006.01)
H01J 49/00 (2006.01)
G01N 30/04 (2006.01)
G01N 30/88 (2006.01)

(52) U.S. Cl.
CPC ... *G01N 30/8665* (2013.01); *G01N 2030/027* (2013.01); *G01N 2030/047* (2013.01); *G01N 2030/8831* (2013.01); *H01J 49/0009* (2013.01)

(58) Field of Classification Search
None
See application file for complete search history.

(56) References Cited

U.S. PATENT DOCUMENTS

| 4,847,493 A | 7/1989 | Sodal et al. |
|---|---|---|
| 6,580,071 B2 | 6/2003 | Weinberger et al. |
| 6,717,134 B2 | 4/2004 | Bowdler |
| 6,734,025 B2 | 5/2004 | Shchepinov |
| 6,908,740 B2 * | 6/2005 | Vandekerckhove ..... C07K 1/36 435/23 |
| 2004/0072251 A1 * | 4/2004 | Anderson .......... G01N 33/6848 435/7.1 |
| 2010/0143938 A1 | 6/2010 | Anderson et al. |

FOREIGN PATENT DOCUMENTS

WO  WO 2014/127144  8/2014

OTHER PUBLICATIONS

Hong et al., "Advances in Size-Exclusion Chromatography for the Analysis of Small Proteins and Peptides: Evaluation of Calibration Curves for Molecular Weight Estimation," Waters Corporation 2012, 6 pages.
Rogers et al., "Our new mixture of 15 heavy peptides streamlines assay design for targeted peptide quantification," Pierce Previews 2011, 4 pages.
Seo et al., "Strategy for Comprehensive Identification of Post-translational Modifications in Cellular Proteins, Including Low Abundant Modifications: Application to Glyceraldehyde-3-phosphate Dehydrogenase," J Proteome Res 2007, 7(2): 587-602.
Sigma-Aldrich Product Information for MS Qual/Quant QC Mix Specification Sheet, 2011, 4 pages.
International Search Report and Written Opinion for PCT/US2014/016289 dated Jul. 28, 2014, 15 pages.
Burkhart et al., "Quality Control of Nano-LC-MS Systems Using Staple Isotope-Coded Pepties," Proteonomics 2011, 11: 1049-1057
Sigma-Aldrich "Mass Spectrometry Use of Proteomic Standards to Optimize Conditions for an MRM LC-MS Platform; MS for Proteins and Peptides; Metabolomics Analysis and the METLIN Metabolite Database," Biofiles 2012, 32 pages.
European Search Report for 14751839.3 dated Feb. 13, 2017, 9 pages.

* cited by examiner

*Primary Examiner* — Thomas S Heard
(74) *Attorney, Agent, or Firm* — Casimir Jones SC; David W. Staple

(57) ABSTRACT

The present invention provides reagents for instrumentation quality control and methods of use thereof. In particular, sets of peptides or other molecules are provided for evaluating the performance of instruments with mass spectrometry (MS) and/or liquid chromatography (LC) functionalities.

18 Claims, 22 Drawing Sheets
Specification includes a Sequence Listing.

| Peptide ## | Sequence | MW | ΔM | SEQ ID. NO.: |
|---|---|---|---|---|
| 1 | LLSLGAGEFK | 1042.0 | 0 | 5 |
| 2 | LLSLGAGEFK | 1049.0 | 7 | 5 |
| 3 | LLSLGAGEFK | 1056.0 | 14 | 5 |
| 4 | LLSLGAGEFK | 1063.0 | 21 | 5 |
| 5 | LLSLGAGEFK | 1073.0 | 31 | 5 |

Figure 5
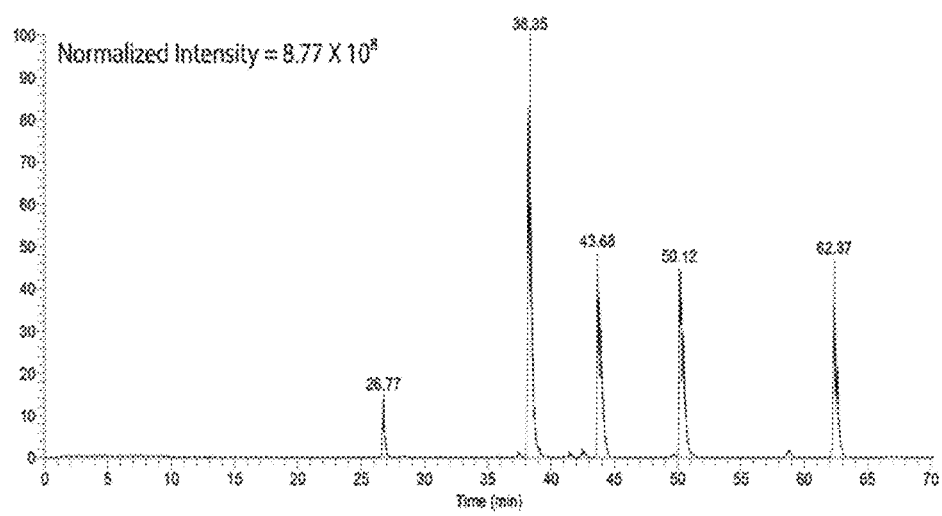
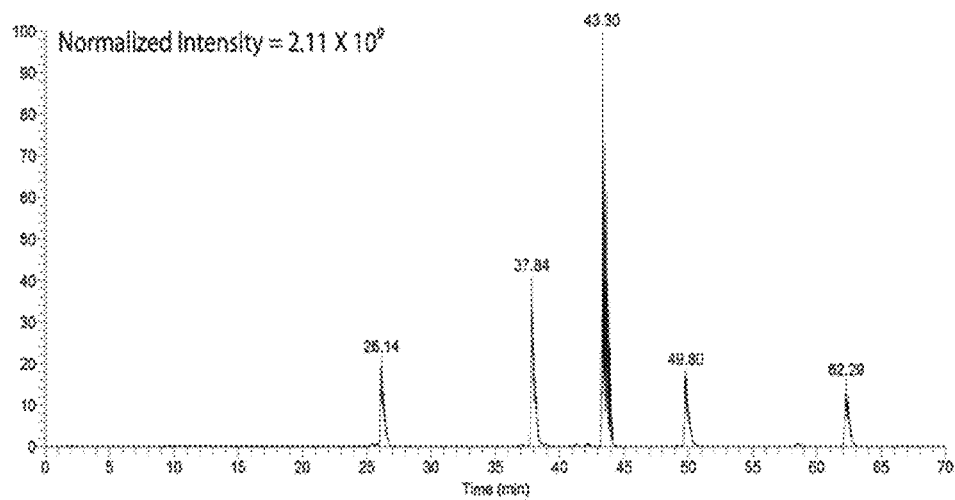

Figure 5 Cont.
All Peptides 1:1:1:1:1 – 15 min Load
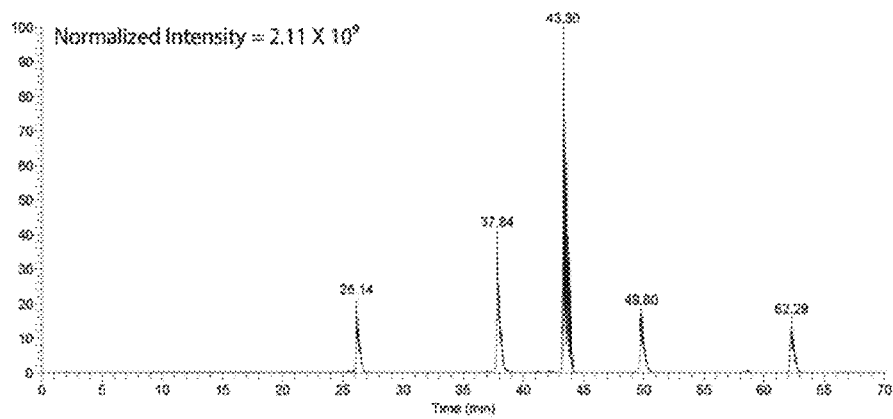
All Peptides 1:1:1:1:1 – 5 min Load
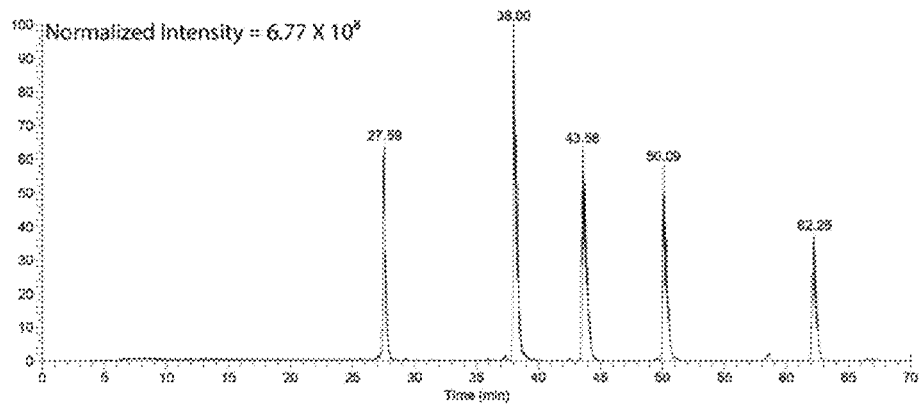
All Peptides 1:1:1:1:1 – 2.5 min Load
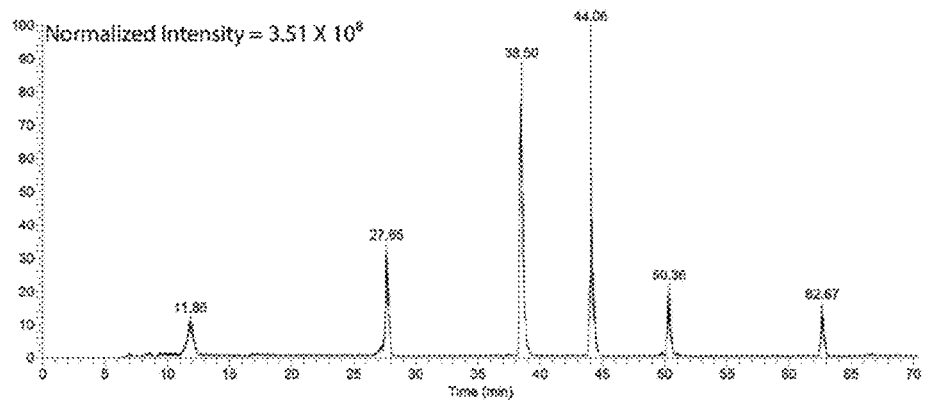

10 Fold Decrease Neat

LLSLGAGEFK (SEQ ID. NO. 5)

QUALITY CONTROL REAGENTS AND METHODS

CROSS-REFERENCE TO RELATED APPLICATIONS

The present application claims priority to U.S. Provisional Patent Application Ser. No. 61/764,312 filed Feb. 13, 2013; which is hereby incorporated by reference in its entirety.

FIELD

The present invention provides reagents for instrumentation quality control and methods of use thereof. In particular, sets of peptides or other molecules are provided for evaluating the performance of instruments with mass spectrometry (MS) and/or liquid chromatography (LC) functionalities.

BACKGROUND

Mass spectrometry provides a rapid and sensitive technique for the determination of the molecular mass of a molecule or mixture of molecules. In the analysis of peptides and proteins, mass spectrometry can provide detailed information regarding, for example, the molecular mass (also referred to as "molecular weight" or "MW") of the original molecule, the molecular masses of peptides generated by proteolytic digestion of the original molecule, the molecular masses of fragments generated during the ionization of the original molecule, and even peptide sequence information for the original molecule and fragments thereof. Mass spectrometers are extremely precise; their performance and calibration must be carefully monitored as systematic errors may cause erroneous m/z values or changes in sensitivity. Methods and kits for the calibration of mass spectrometers have been described in various patents and applications (See, e.g., U.S. Pat. No. 4,847,493; U.S. Patent Application Publication No. 2002/0033447; U.S. Patent Application Publication No. 2002/0045269; U.S. Patent Application Publication No. 2003/0062473) and are also commercially available (See, e.g., PROTEOMASS Peptide and Protein MALDI-MS Calibration Kit (Sigma-Aldrich, St. Louis, Mo., USA); Mass Standards Kit (Applied Biosystems, Foster City, Calif., USA); MASSPREP reference standards (Waters, Milford, Mass., USA); Protein Calibration Standard 120,000-70,000 Da (Bruker Daltonics, Billerica, Mass., USA); All-in-1 Protein Standard (Ciphergen, Fremont, Calif., USA)). However, these kits do not directly provide a measure of instrument sensitivity or dynamic range in a single run.

SUMMARY

In some embodiments, the present invention provides reagents comprising two or more distinct-mass versions of each of two or more distinct-structure (e.g., sequence) molecules (e.g., peptide, nucleic acid, peptide nucleic acid, polymer, etc.). Although many embodiments of the present invention are described as comprising or for use with peptide reagents, these embodiments should be viewed more broadly as applying to quality control and performance evaluation reagents comprising other molecules and/or polymers. In some embodiments, the present invention is not limited to peptide reagents.

In some embodiments, the present invention provides peptide mixtures comprising two or more distinct-mass versions of each of two or more distinct-sequence peptides. In some embodiments, the present invention provides peptide mixtures consisting of, or consisting essentially of, two or more distinct-mass versions of each of two or more distinct-sequence peptides. In some embodiments, each of the distinct-sequence peptides is of distinct hydrophobicity. In some embodiments, all of the distinct-mass versions of any of the distinct-sequence peptides are present at distinct concentrations. In some embodiments, the distinct-mass versions of any of the distinct-sequence peptides are present at concentrations ranging from at least as low as 0.1 nM to at least as high at 100 µM. In some embodiments, the distinct-mass versions of any of the distinct-sequence peptides are present at concentrations ranging from 1 nM to 10 µM. In some embodiments, the distinct-mass versions of any of the distinct-sequence peptides are present in a reagent at zeptomoles to picomoles of total peptide. In some embodiments, the distinct-sequence peptides are separable by liquid chromatography based on their different hydrophobicities or other chemical properties (e.g., charge, size, or hydrophilicity). In some embodiments, a peptide mixture comprises 3-20 distinct-sequence peptides. In some embodiments, a peptide mixture comprises 5-10 distinct-sequence peptides. In some embodiments, the distinct-mass versions of any of the distinct-sequence peptides are differentiable by mass spectrometry. In some embodiments, the distinct-mass versions of any of the distinct-sequence peptides are the result of different combinations of stable isotope-labeled amino acids. In some embodiments, the distinct-mass versions of any of the distinct-sequence peptides are the result of different combinations of stable isotope of constituent atoms. In some embodiments, each of the distinct-mass versions of any of the distinct-sequence peptides comprises a different number of uniformly stable isotope-labeled amino acids. In some embodiments, a peptide mixture comprises 3-20 distinct-mass versions of each of the distinct-sequence peptides. In some embodiments, a peptide mixture comprises 5-10 distinct-mass versions of each of the distinct-sequence peptides.

In some embodiments, the present invention provides methods for assessing performance of an instrument with both liquid chromatography (LC) and mass spectrometry (MS) functionalities comprising: (a) introducing a peptide mixture to the instrument, wherein said peptide mixture comprises two or more distinct-mass versions of each of two or more distinct-sequence peptides; (b) analyzing the peptide mixture by LC (consisting of various mobile phases, including but not limited to $C_{18}$, SCX, HILIC etc.); (c) analyzing the peptide mixture by MS (consisting of but not limited to ESI or MALDI methods of ionization); and (d) assessing the performance of the LC and MS functionalities of the instrument based on results of steps (b) and (c). In some embodiments, the peptide mixture purified peptides. In some embodiments, the purified peptides of the peptide miXture are the only peptides introduced to the instrument in step (a). In some embodiments, the peptide mixture comprises peptides in the presence of one or more impurities. In some embodiments, the peptide mixture is introduced to the instrument in the presence of one or more other peptides (e.g., background, contaminants, etc.). In some embodiments, the peptide mixture is a peptide mixture that comprises two or more distinct-mass versions of each of two or more distinct-sequence peptides. In some embodiments, assessing the performance of the LC and MS functionalities of the instrument comprises reporting one or more LC-parameters for each peptide sequence selected from: retention times, peak height, peak width, peak resolution, and peak symmetry or one or more MS-parameters selected from mass accuracy, mass resolution, sensitivity, dynamic range, linear response, MS/MS spectral quality and sampling and/or isolation efficiency. In some embodiments, assessing the performance of the LC and MS functionalities of the instrument comprises reporting one or more MS-parameters for each distinctly-massed version of one or more of the peptide sequences selected from: resolution, mass accuracy, and sensitivity as a "neat" mixture, sensitivity within a complex mixture, instrumental sampling, and dynamic range. In some embodiments, the assessment of LC and/or MS performance is provided by a software program. In some embodiments, the software reports LC and/or MS parameters from a single analysis, the performance history of the instrument or a comparison between multiple LC and/or MS instruments or instrument platforms. In some embodiments, the software provides a performance score of the LC and/or MS instrument. In some embodiments, sensitivity and/or performance are evaluated for a neat sample (e.g., reagent without substantial background causing agents). In some embodiments, sensitivity and/or performance are evaluated for a complex sample (e.g., reagent and background causing agents/peptides).

In some embodiments, the present invention provides methods for assessing performance of an instrument with both liquid chromatography (LC) and mass spectrometry (MS) functionalities comprising: (a) introducing a peptide mixture to the instrument, wherein said peptide mixture comprises two or more distinct-mass versions of each of two or more distinct-sequence peptides, wherein said peptide mixture comprises two or more distinct-mass versions of each of two or more distinct-sequence peptides; (b) analyzing the peptide mixture by LC; (c) analyzing the peptide mixture by MS; and (d) assessing the performance of the LC and MS functionalities of the instrument based on results of steps (b) and (c). In some embodiments, distinct-sequence peptides are of distinct hydrophobicities and separable by LC. In some embodiments, the present invention provides distinct-mass versions that comprise different combinations of heavy isotope labeled amino acids and are resolved by MS. In some embodiments, the assessment of LC and MS performance is provided by a software program. In some embodiments, the software reports LC and MS parameters from a single analysis, the performance history of the instrument or a comparison between multiple LC and MS instruments. In some embodiments, the software provides a performance score of the LC and/or MS instrument.

In some embodiments, the present invention provides reagents and/or methods for quality control and/or evaluating the performance of instruments with mass spectrometry (MS) and/or liquid chromatography (LC) functionalities. In some embodiments, both MS and LC functionalities are assessed. In some embodiments, only one of MS and LC functionalities are assessed. In some embodiments, an instrument has both MS and LC functionalities, but only one is assessed. In some embodiments, an instrument has only one of MS and LC functionalities. In some embodiments, MS and LC functionalities are provided by a single unit. In some embodiments, MS and LC functionalities are provided by separate units.

In some embodiments, the assessment of the performance of LC and/or MS functionality is performed by software. In some embodiments, the software generates a performance score. In some embodiments, a performance score is unique to the tested instrument (or type of instrument tested). In some embodiments, a performance score can be used for assessment of the tested instrument (or type of instrument tested) at a given time and/or over time. In other embodiments, a performance score is comparable to performance scores of other similar and/or different instruments (e.g., those with LC and/or MS functionality). In some embodiments, a performance score can be used for comparison of a tested instrument (or type of instrument tested) to other similar and/or different instruments at a given time and/or over time. In some embodiments, software is used to track an instruments historical performance. In some embodiments, a report of instrument performance parameters (e.g., score) is generated.

In some embodiments, the present invention provides methods for assessing performance of an instrument with both liquid chromatography (LC) and mass spectrometry (MS) functionalities comprising: (a) introducing (e.g., injecting) a peptide mixture to the instrument, wherein the peptide mixture comprises two or more distinct-mass versions of each of two or more distinct-sequence peptides; (b) separating or analyzing the peptide mixture by LC; (c) analyzing the peptide mixture by MS; and (d) assessing the performance of the LC and MS functionalities of the instrument based on results of steps (b) and (c) using software. In some embodiments, the peptide mixture is a peptide mixture that comprises two or more distinct-mass versions of each of two or more distinct-sequence peptides. In some embodiments, each distinct-mass version of a distinct-sequence peptide is present at a different concentration. In some embodiments, assessing the performance of the LC and MS functionalities of the instrument comprises reporting one or more LC-parameters for each peptide sequence selected from: retention times, peak height, peak width, peak resolution, and peak symmetry. In some embodiments, assessing the performance of the LC and MS functionalities of the instrument comprises reporting one or more MS-parameters for each distinctly-massed versions of one or more of the peptide sequences selected from: resolution, mass accuracy, sensitivity of "neat" samples, sensitivity within complex samples, dynamic range, mass resolution, isolation efficiency, MS/MS spectral quality and linear response in a single analytical experiment. In some embodiments, performance is assessed by software which generates a performance score.

BRIEF DESCRIPTION OF THE DRAWINGS

FIG. 5 shows graphs depicting the effect of loading time on the binding of the peptides to the LC column.

DEFINITIONS

Figure 1:
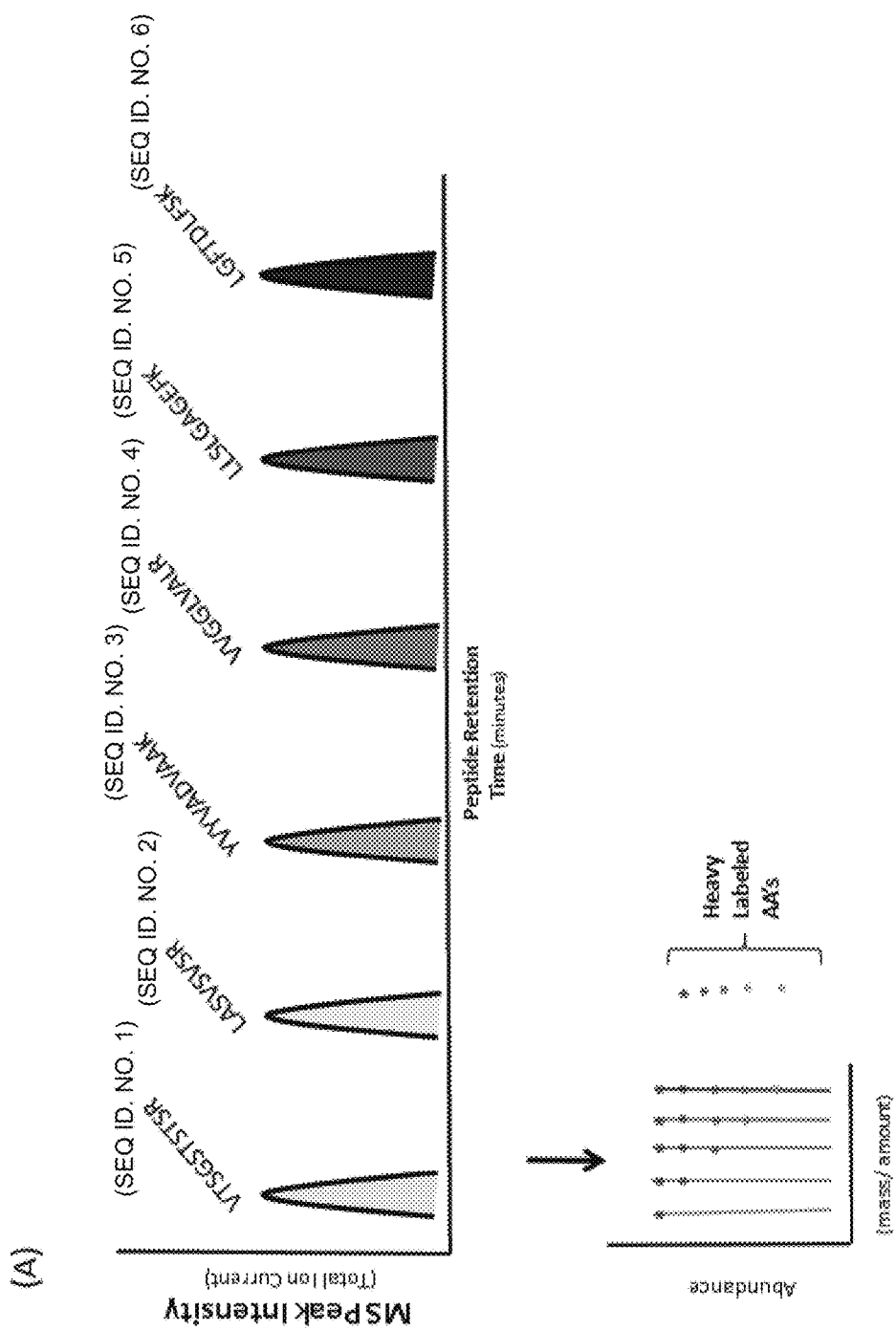
FIG. 1 shows an illustration of a chromatogram (top panel) of a reagent comprising six distinct-sequence peptides, and a mass spectrum (bottom panel) of one of those distinct-sequence peptides which is made up of 5 distinct-mass versions. The distinct-sequence peptides are designed to be spaced (relatively) evenly across a standard chromatographic gradient when analyzed, for example, on a $C_{18}$ reversed phase column using an acetonitrile/0.1% organic acid (like Formic acid or trifluoroacetic acid) gradient. From a chromatographic standpoint it would appear that the product only contains six peptides. However, mass spectra reveal that each peak corresponding to a peptide sequence corresponds to five isomeric peptides which, although identical in sequence, are clearly distinguished by a mass spacing of at least 4 Daltons.
Figure 2:
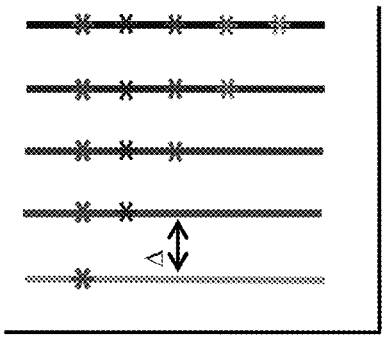
FIG. 2 shows a table of five distinct-mass versions of a peptide sequence and their respective masses (right). An exemplary mass spectrum for these peptides is provided (left). In some embodiments, mass spacing of 7-10 Daltons is provided, allowing for spacial resolution in both high and low-resolution MS instruments. In order to achieve this mass differentiation (i.e. distinct-mass variants) stable, heavy isotopically enriched amino acids are incorporated.
Figure 3:
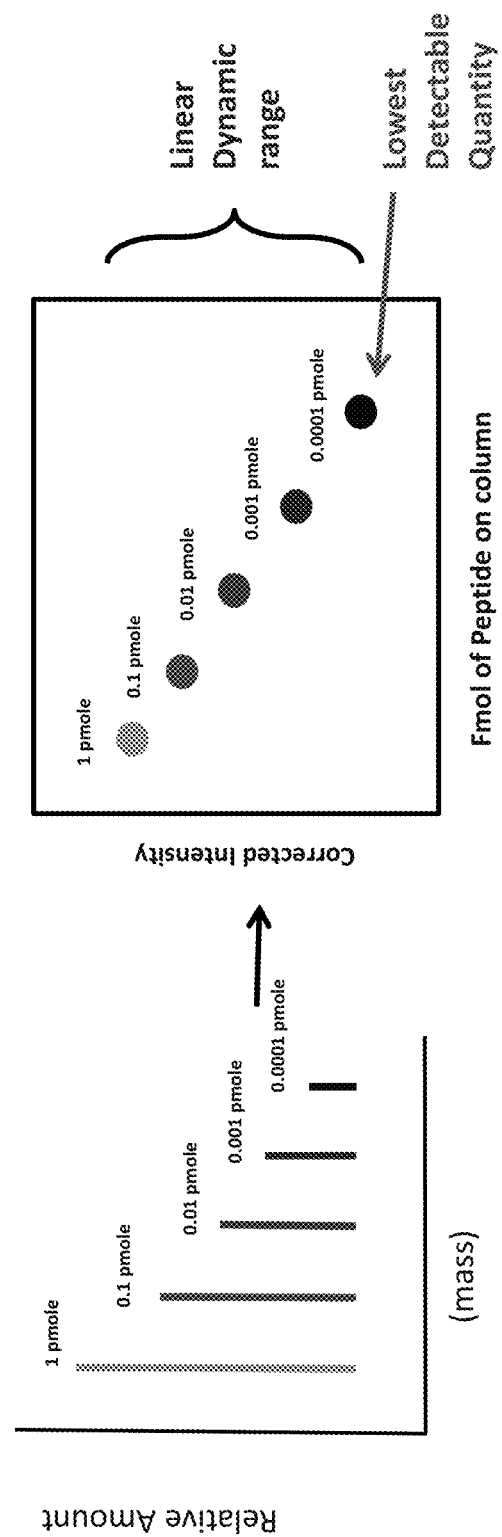
FIG. 3 shows an illustration of an embodiment of the present invention in which distinct-mass versions of a peptide sequence are provided at different concentrations. Because their quantities are precisely known, individual (distinct mass) peptides can be mixed in ratios such that a plot of relative intensity versus the molar amount on column is linear when plotted as the log (fold-difference) of the corrected intensity. In the example provided, the lightest peptide (i.e. the peptide with only one heavy labeled amino acid) is the most abundant. Each successively heavy peptide is 10× lower in concentration, thus giving the desired linear relationship.
Figure 4:
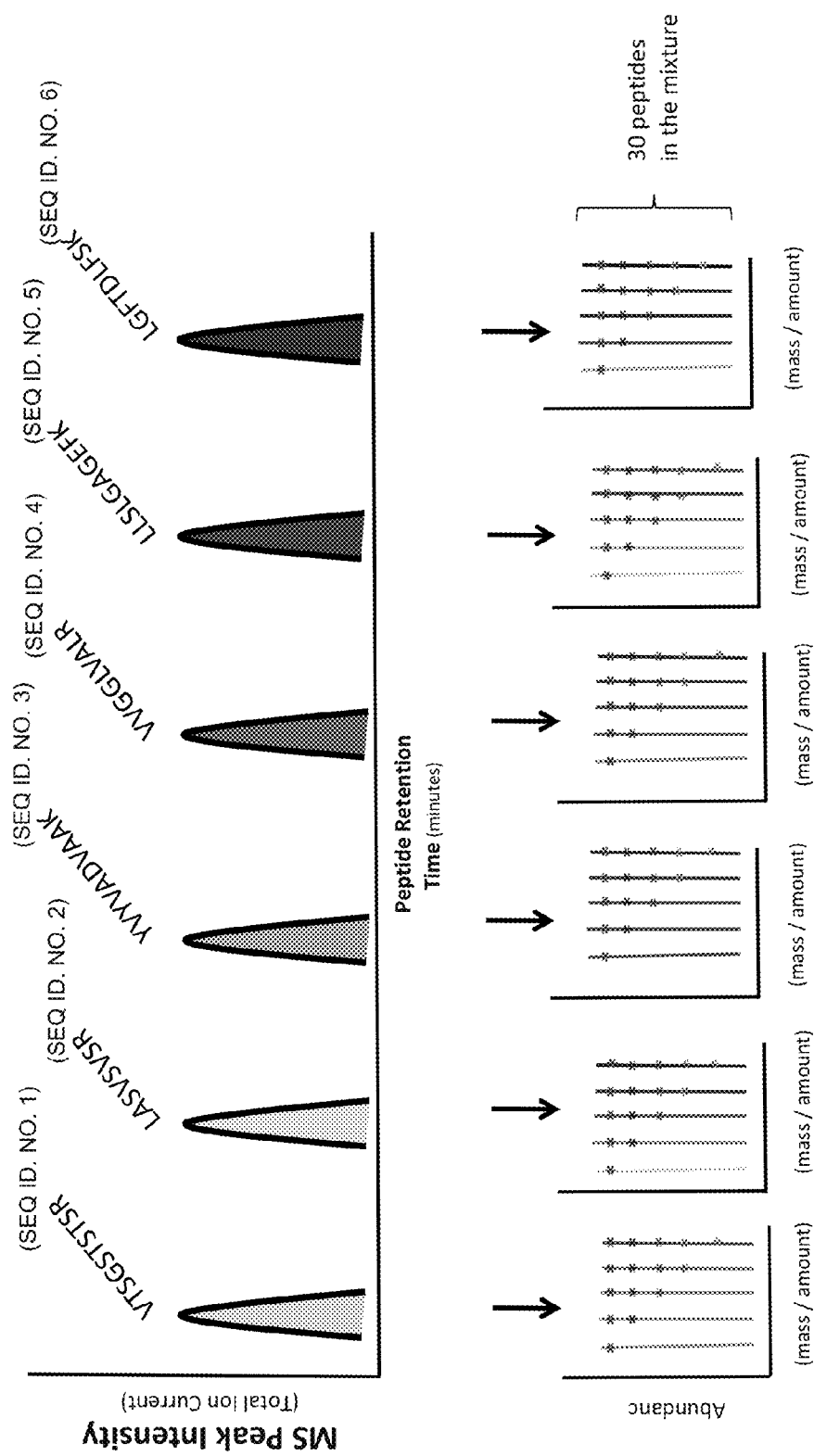
FIG. 4 shows an illustration of an embodiment of the invention comprising five distinct-mass versions of each of six distinct-sequence peptides. The top panel depicts a chromatogram of the reagent, in which distinct peaks are visible for each of the distinct sequences. The lower panel depicts mass spectra for each sequence, in which each distinct mass version is separately identifiable. Thus, the whole mixture is a 30 peptide mixture, in this embodiment.

As used herein, unless otherwise specified, the term "peptide" refers to a polymer compound of two or more amino acids joined through the main chain by peptide amide bonds (—C(O)NH—). When used in conjunction with, or in comparison to, the term "polypeptide," the term "peptide" typically refers to short amino acid polymers (e.g., chains having fewer than 25 amino acids), whereas the term "polypeptide" refers to longer amino acid polymers (e.g., chains having more than 25 amino acids).

As used herein, the term "distinct-sequence peptides" refers to a group of peptides (e.g., two or more) that can be differentiated from one another by the identity and/or order of their amino acids. For example, 'three distinct-sequence peptides' are three amino acid chains that, although possibly sharing other characteristics, each comprise at least one amino acid difference, and possibly many amino acid differences, from each other (e.g., LLSLGALEFK (SEQ ID NO: 7), LSSLGALEFK (SEQ ID NO: 8), and AAPGED-SRKY (SEQ ID NO: 9)).

As used herein, the term "distinct-mass peptides" refers to a group of peptides (e.g., two or more) that can be differentiated from one another by mass, even if they cannot be differentiated by sequence. "Distinct-mass versions of a peptide" refers to a group of peptides that can be differentiated from one another by mass, even though they cannot be differentiated by amino acid sequence (e.g., peptides have the same amino acid sequence). For example, 'three distinct-mass versions of a peptide' are three amino acid chains that, although having the same amino acid sequence, are tagged or labeled (e.g., stable heavy isotope labeled) to have different masses (e.g., LLSLGALEFK (SEQ ID NO: 7), L*LSLGALEFK (SEQ ID NO: 7), and L*L*SLGALEFK (SEQ ID NO: 7); wherein * indicates uniform isotopic labeling of the preceding amino acid).

As used herein, the term "isomeric peptides" refers to a group of peptides (e.g., two or more) that have the same amino acid sequence. The peptides do not differ in terms of tags or chemical modifications, but typically contain varying degrees of stable, heavy isotope labeling (e.g. $^{13}$C, $^{15}$N, $^{18}$O, $^{2}$H, etc.). A pair of isomeric peptides may differ in the number of uniformly $^{13}$C/$^{15}$N-labeled amino acids they contain. For example, L*LSLGALEFK (SEQ ID NO: 7) and L*L*SLGA*LEFK (SEQ ID NO: 7) (* indicates uniform $^{13}$C/$^{15}$N labeling of the preceding amino acid) are isomeric peptide (they are also 'distinct-mass peptides' and 'distinct-mass versions of a peptide with the sequence LLSLGALEFK (SEQ ID NO: 7)).

As used herein, the term "heavy," refers to an isotope of an element that has a higher molecular mass than the isotope that is most prevalent at natural abundance (e.g., $^{13}$C instead of $^{12}$C, $^{2}$H instead of $^{1}$H, $^{15}$N instead of $^{14}$N, $^{18}$O instead of $^{16}$O, etc.), or any chemical entities (e.g., peptides, molecules, etc.) comprising one or more of such isotopes.

As used herein, the term "uniformly heavy labeled" refers to a molecular entity (e.g., peptide, amino acid, etc.) in which substantially all of one or more elements within the molecular entity are present as a heavy isotope instead of the isotope that is most prevalent at natural abundance. For example, uniformly $^{13}$C/$^{15}$N-labelled amino acid is one in which substantially all the carbons and nitrogens (e.g., >95%, >98%, >99%, >99.9%) are present as $^{13}$C instead of $^{12}$C and $^{15}$N instead of $^{14}$N. In some embodiments, a "heavy labeled peptide" may comprise one or more uniformly heavy labeled amino acids.

DETAILED DESCRIPTION

The present invention provides reagents for instrumentation quality control and methods of use thereof. In particular, sets of peptides or other molecules are provided for evaluating the performance of instruments with mass spectrometry (MS) and/or liquid chromatography (LC) functionalities.

In particular embodiments, provided herein are reagents for calibration, performance evaluation, performance monitoring, system suitability, quality control (QC), etc. of analytical instruments (e.g., HPLC (with UV or other modes of detection), MS, LC-MS, etc.). In some embodiments, a QC reagent comprises a set of peptides that can be predictably separated and/or analyzed by LC, MS, or both. In some embodiments, peptides of reagents provided herein exhibit a broad range of hydrophobicities or other chemical characteristics such that they can be used to probe the entire separation range of an LC instrument. In some embodiments, peptide reagents provided herein exhibit a broad range of masses such that they can be used to probe the mass/charge (m/z) ratio range of an MS instrument. In some embodiments, by reviewing the analysis of a reagent of the present invention (e.g., manually or automated by software), the performance of the analyzing instrument is evaluated. By comparing present and past performance evaluations (e.g., relative to the same peptide reagent), changes in instrument performance can be identified, monitored, and/or recorded over periods of time ranging from days to months.

In certain embodiments, the present invention provides reagents comprising two or more distinct-sequence peptides (e.g., 2 sequences, 3 sequences, 4 sequences, 5 sequences, 6 sequences, 7 sequences, 8 sequences, 8 sequences, 10 sequences . . . 15 sequences . . . 20 sequences . . . 25 sequences . . . 30 sequences . . . 50 sequences, or more). In certain embodiments, reagents comprise three or more distinct-sequence peptides, four or more distinct-sequence peptides, five or more distinct-sequence peptides, six or more distinct-sequence peptides, seven or more distinct-sequence peptides, eight or more distinct-sequence peptides, nine or more distinct-sequence peptides, ten or more distinct-sequence peptides, twelve or more distinct-sequence peptides, fifteen or more distinct-sequence peptides, twenty or more distinct-sequence peptides, etc.

In some embodiments, each peptide sequence of a group of distinct-sequence peptides is of a detectably different hydrophobicity. In certain embodiments, each peptide sequence of a group of distinct-sequence peptides has a unique hydrophobicity (e.g., each peptide is separable from all of the others by LC). In other embodiments, one or more peptide sequence of a group of distinct-sequence peptides has a unique hydrophobicity (e.g., one or more, but not all, peptides are separable from all of the others by LC). In some embodiments, the differences in hydrophobicity can be detected by liquid chromatography (e.g., high performance liquid chromatography (HPLC)). In certain embodiments, each distinct-sequence peptide results in a chromatography peak that is distinguishable from the peaks of the other distinct-sequence peptide. In some embodiments, the distinct-sequence peptides span a hydrophobicity range such that they can all be distinguished (e.g., separated) on a single run through a LC column.

In some embodiments, distinct-mass versions of a peptide are provided. In some embodiments, two or more distinct-mass, same-sequence peptides are provided. In particular embodiments, distinct-mass versions of the same peptide sequence comprise different isotopic labeling. For example, distinct-mass versions of the same peptide sequence may comprise different degrees of heavy isotope labeling. In certain embodiments, all, or a portion of, the amino acids in a peptide comprise amounts above natural abundance levels of heavy isotopes (e.g., $^{2}$H, $^{13}$C, $^{15}$N, $^{18}$O, etc.). In some embodiments, same sequence peptides have different masses based on the degree of heavy isotope labeling of all or a portion of their amino acids (e.g., all amino acids in a peptide at natural abundance, all amino acids in a peptide 25% $^{13}$C/$^{15}$N-labelled, all amino acids in a peptide 50% $^{13}$C/$^{15}$N-labelled, all amino acids in a peptide 75% $^{13}$C/$^{15}$N-labelled, all amino acids in a peptide >99% $^{13}$C/$^{15}$N-labelled, etc.). In other embodiments, same-sequence peptides have different masses based on the number of fully (e.g., uniformly $^{13}$C/$^{15}$N labeled) heavy isotope labeled amino acids in the respective peptides (e.g., 0 amino acids uniformly labeled, 1 amino acid uniformly labeled, 2 amino acids uniformly labeled, 3 amino acids uniformly labeled, 4 amino acids uniformly labeled, 5 amino acids uniformly labeled, 6 amino acids uniformly labeled, or more). In some embodiments, differences in mass of the same sequence peptides result from a combination of the number of isotopically-labeled amino acids and the degree to which they are labeled (3 amino acids are 50% $^{13}$C/$^{15}$N-labelled, all amino acids have 99% non-exchangeable $^{2}$H labeled, 6 amino acids 75% $^{18}$O labeled, etc.). Mass-tags and other labels or modifications may also be employed to alter the mass of peptides without changing the amino acid sequence.

In some embodiments, two or more distinct-mass versions of a single peptide sequence are provided. In some embodiments, two or more (e.g., 2, 3, 4, 5, 6, 7, 8, 9, 10, or more) distinct-mass versions of each of a plurality (e.g., 2, 3, 4, 5, 6, 7, 8, 9, 10, or more) of distinct-sequence peptides are provided.

In various embodiments, the distinct-mass versions of a peptide (e.g., a distinct-sequence peptide) are not distinguishable by liquid chromatography (e.g., all distinct-mass versions of a peptide elute from a chromatography column (e.g., HPLC column) in a single peak). In various embodiments, all distinct-mass versions of a peptide sequence exhibit substantially identical hydrophobicity. In some embodiments isomeric peptides have identical or substantially identical hydrophobicities and elute from a chromatography column (e.g., HPLC column) in a single peak.

In some embodiments, a set (e.g., 2, 3, 4, 5, 6, 7, 8, 9, 10, or more) of distinct-mass isomeric peptides are provided. In some embodiments, each isomer has the same or substantially the same hydrophobicity and co-elutes from liquid chromatography (e.g., HPLC). In some embodiments, each isomer contains a distinct pattern (e.g., different number) of stable isotope labeling (e.g., different combination of uniform $^{13}C/^{15}N$ labeled amino acids), and can therefore be distinguished by mass spectrometry. In some embodiments, a distinct-mass isomer in a set is provided at any suitable concentration (e.g., 10 pM . . . 100 pM . . . 1 nM . . . 10 nM . . . 100 nM . . . 1 μM . . . 10 μM . . . 100 μM). Distinct-mass isomers may be of unique concentrations or may be at the same concentration as one or more other distinct-mass peptides of the same set. In certain embodiments, each distinct-mass isomer in a set is provided at the same concentration (e.g., 10 pM . . . 100 pM . . . 1 nM . . . 10 nM . . . 100 nM . . . 1 μM . . . 10 μM . . . 100 μM). In other embodiments, each distinct-mass isomer in a set is provided at a different concentration (e.g., a set of five distinctly-massed isomers provided at 1 nM, 10 nM, 100 nM, 1 μM, and 10 μM, respectively).

In some embodiments, the present invention provides two or more (e.g., 2, 3, 4, 5, 6, 7, 8, 9, 10, or more) distinct-sequence sets of two or more (e.g., 2, 3, 4, 5, 6, 7, 8, 9, 10, or more) distinct-mass isomeric peptides. Table 1 depicts generic peptides comprising six distinct-sequence sets (sequences A-F) of four distinct-mass versions each (0, 1, 2, or 3 labeled amino acids).

TABLE 1

Generic distinct-sequence sets of distinct-mass isomeric peptides.

| Amino Acid Sequence | Number of uniformly labeled amino acids |
|---|---|
| Sequence A | 0 |
| Sequence A | 1 |
| Sequence A | 2 |
| Sequence A | 3 |
| Sequence B | 0 |
| Sequence B | 1 |
| Sequence B | 2 |
| Sequence B | 3 |
| Sequence C | 0 |
| Sequence C | 1 |
| Sequence C | 2 |
| Sequence C | 3 |
| Sequence D | 0 |
| Sequence D | 1 |
| Sequence D | 2 |
| Sequence D | 3 |
| Sequence E | 0 |
| Sequence E | 1 |
| Sequence E | 2 |
| Sequence E | 3 |
| Sequence F | 0 |
| Sequence F | 1 |
| Sequence F | 2 |
| Sequence F | 3 |

While Table 1 depicts 0-3 labeled amino acids per sequence, sets with greater number of labeled amino acids are contemplated (e.g., 0-5, 0-10, etc.). In some embodiments, the distinct-sequence peptides of a reagent may each be present as the same number of distinct-mass versions (as depicted in Table 1). In other embodiments, two or more distinct-sequence peptides of a reagent comprise different numbers of distinct-mass versions.

Table 2 depicts an embodiment of the invention which comprises six distinct sequence sets (VTSGSTSSR (SEQ ID NO: 1), LASVSVSR (SEQ ID NO: 2), YVYVADVAAK (SEQ ID NO: 3), VVGGLVALR (SEQ ID NO: 4), LLSLGAGEFK (SEQ ID NO: 5), LGFTDLFSK (SEQ ID NO: 6)) of six distinct mass isomeric peptides each.

TABLE 2

Exemplary distinct-sequence sets of distinct-mass isomeric peptides.

| Set | distinct-sequence peptides | distinct-mass isomers | SEQ ID NO: | Set | distinct-sequence peptides | distinct-mass isomers | SEQ ID NO: |
|---|---|---|---|---|---|---|---|
| 1 | VTSGSTSSR | V*T*S*GST*ST*SR* | 1 | 4 | VVGGLVALR | V*V*GGL*V*ALR* | 4 |
| 1 | | V*T*SGSTST*SR* | 1 | 4 | | V*V*GGLV*ALR* | 4 |
| 1 | | V*T*SGSTSTSR* | 1 | 4 | | V*V*GGLVALR* | 4 |
| 1 | | V*TSGSTSTSR* | 1 | 4 | | V*VGGLVALR* | 4 |
| 1 | | VTSGSTSTSR* | 1 | 4 | | VVGGLVALR* | 4 |
| 1 | | VTSGSTSTSR | 1 | 4 | | VVGGLVALR | 4 |
| 2 | LASVSVSR | L*A*SV*SV*S*R* | 2 | 5 | LLSLGAGEFK | L*L*SL*GAGEF*K* | 5 |
| 2 | | L*ASV*SV*SR* | 2 | 5 | | L*L*SL*GAGEFK* | 5 |
| 2 | | LASV*SV*SR* | 2 | 5 | | L*L*SLGAGEFK* | 5 |
| 2 | | LASVSV*SR* | 2 | 5 | | L*LSLGAGEFK* | 5 |

TABLE 2-continued

Exemplary distinct-sequence sets of distinct-mass isomeric peptides.

| Set | distinct-sequence peptides | distinct-mass isomers | SEQ ID NO: | Set | distinct-sequence peptides | distinct-mass isomers | SEQ ID NO: |
|---|---|---|---|---|---|---|---|
| 2 | | LASVSVSR* | 2 | 5 | | LLSLGAGEFK* | 5 |
| 2 | | LASVSVSR | 2 | 5 | | LLSLGAGEFK | 5 |
| 3 | YVYVADVAAK | YV*YV*ADV*A*A*K* | 3 | 6 | LGFTDLFSK | L*GF*TDL*F*SK* | 6 |
| 3 | | YV*YV*ADV*AAK* | 3 | 6 | | L*GFTDL*F*SK* | 6 |
| 3 | | YVYV*ADV*AAK* | 3 | 6 | | L*GFTDL*FSK* | 6 |
| 3 | | YVYVADV*AAK* | 3 | 6 | | L*GFTDLFSK* | 6 |
| 3 | | YVYVADVAAK* | 3 | 6 | | LGFTDLFSK* | 6 |
| 3 | | YVYVADVAAK | 3 | 6 | | LGFTDLFSK | 6 |

*indicates uniform $^{13}$C/$^{15}$N labeling of the preceding amino acid)

The distinct-sequence sets exhibit varying degrees of hydrophobicity, and therefore each set elutes independently when analyzed by liquid chromatography (e.g., HPLC). Each distinct-mass isomer of a distinct-sequence set has the same hydrophobicity, and therefore co-elute when analyzed by liquid chromatography (e.g., HPLC). Any other suitable combinations of distinct-sequence sets of distinct-mass isomers are within the scope of the present invention. In some embodiments, the invention is not limited by the length, sequence, number, or labeling of the peptides.

In some embodiments, peptides within a set of distinct sequence peptides are selected based on criteria including, but not limited to: peak intensity, peak width, peak compactness (narrowness), LC retention time (e.g., not overlapping with another peptide in the reagent), absence of excluded amino acids (e.g., P, M, W, C, N, Q, and/or N-terminal E) which are deemed to contribute to product instability, feasibility of incorporating sufficient number (e.g., 2, 3, 4, 5, 6, 7, 8, 9, 10, or more) of stable, isotope labeled amino acids (e.g., commercially available stable isotope labeled amino acids), stability, ease of achieving high degree (e.g., >90%, >91%, >92%, >93%, >94%, >95%, >96%, >97%, >98%, >99%) of purity, etc. In some embodiments, peptides comprise one or more uniformly isotopically $^{13}$C/$^{15}$N labeled amino acids, for example, those selected from Table 3.

TABLE 3

Exemplary universally $^{13}$C/$^{15}$N labeled amino acids

| Three Letter Code | Single Letter Code | Molecular formula of 13C/15N universally-labeled free amino acid | Molecular formula of 13C/15N universally-labeled amino acid residues | Mass shift relative to unlabeled |
|---|---|---|---|---|
| Ala | A^ | (13C)3H7(15N)O2 | (13C)3H5(15N)O | (+4) |
| Arg | R^ | (13C)6H14(15N)4O2 | (13C)6H12(15N)4O | (+10) |
| Asn | N^ | (13C)4H8(15N)2O3 | (13C)4H6(15N)2O2 | (+6) |
| Asp | D^ | (13C)4H7(15N)O4 | (13C)4H5(15N)O3 | (+5) |
| Cys | C^ | (13C)3H7(15N)O2S | (13C)3H5(15N)OS | (+4) |
| Gln | Q^ | (13C)5H10(15N)2O3 | (13C)5H8(15N)2O2 | (+7) |
| Glu | E^ | (13C)5H9(15N)O4 | (13C)5H7(15N)O3 | (+6) |
| Gly | G^ | (13C)2H5(15N)O2 | (13C)2H3(15N)O | (+3) |
| Ile | I^ | (13C)6H13(15N)O2 | (13C)6H11(15N)O | (+7) |
| Leu | L^ | (13C)6H13(15N)O2 | (13C)6H11(15N)O | (+7) |
| Lys | K^ | (13C)6H14(15N)2O2 | (13C)6H12(15N)2O | (+8) |
| Met | M^ | (13C)5H11(15N)O2S | (13C)5H9(15N)OS | (+6) |
| Phe | F^ | (13C)9H11(15N)O2 | (13C)9H9(15N)O | (+10) |
| Pro | P^ | (13C)5H9(15N)O2 | (13C)5H7(15N)O | (+6) |
| Ser | S^ | (13C)3H7(15N)O3 | (13C)3H5(15N)O2 | (+4) |
| Thr | T^ | (13C)4H9(15N)O3 | (13C)4H7(15N)O2 | (+5) |
| Tyr | Y^ | (13C)9H11(15N)O3 | (13C)9H9(15N)O2 | (+10) |
| Val | V^ | (13C)5H11(15N)O2 | (13C)5H9(15N)O | (+6) |

In some embodiments, provided herein is a reagent (e.g., peptide mixture), and methods of use thereof, for the validation, calibration, performance assessment, and/or performance monitoring of analytic instruments (e.g., liquid chromatographs with UV and/or MS detection). In some embodiments, a reagent provides a performance meter that is used to monitor instrument performance. Reagents and methods provide: assessment of initial instrument performance, monitoring of instrument history, comparison of parameters between instruments, validation of instrument performance (e.g., before or after use), etc.

In some embodiments, a reagent comprises a plurality (e.g., 5) of distinct-sequence sets of several (e.g., 5) distinct-mass isomeric peptides each. The reagent is analyzed by liquid chromatography, which separates each of the distinct-sequence sets from each other by their different hydrophobicities. The reagent is subsequently analyzed by mass spectrometry, which characterizes the distinct-mass isomers within each set by their mass-to-charge ratios. The mass differences (e.g., 3-5 Daltons) between the same-sequence isomers are apparent from such MS-characterization. In some embodiments, the different isomers within a set are provided at a range of different concentrations. The concentration differences among the isomers within each set are apparent based on the MS analysis and/or amino acid analysis. In some embodiments, analysis of a single reagent by both the LC and MS components of an instrument provides simultaneous performance analysis. In other embodiments, a reagent is first analyzed by LC and then analyzed by MS. In some embodiments, a reagent is analyzed by LC and MS simultaneously (e.g., two portions of the same reagent are each subjected to analysis by one technique).

In some embodiments, all the peptides in a reagent are provided at the same concentration. In some embodiments, each distinct-mass version of a peptide sequence is the same concentration. In some embodiments, each distinct-mass version of a peptide sequence is a different concentration. In some embodiments, the distinct-mass versions of a peptide sequence are provided at a range of concentrations. In particular embodiments, the distinct-mass versions of each peptide sequence in a reagent are provided at the same range of concentrations. In some embodiments, each distinct-sequence peptide (e.g. the sum of the distinct-mass version of the same peptide sequence) is provided at the same concentration. In some embodiments, each distinct-sequence peptide (e.g. the sum of the distinct-mass version of the same peptide sequence) is provided at a unique concentration. In some embodiments, the distinct-sequence peptides (e.g. the sum of the distinct-mass version of the same peptide sequence) are provided at range of concentrations (e.g., linear or non-linear distribution over a range).

In some embodiments, a reagent comprises buffers, solvents, salts, and/or other additives (e.g., marker (e.g., radio-label, fluorescent dye, chromophore, mass tag, etc.), etc.) suitable for use in LC and/or MS. Reagents may comprise any suitable buffer (e.g., suitable for use in both LC and MS), such as Ammonium Bicarbonate, Triethyl ammonium bicarbonate (TEAB), TAPS, Tris, HEPES, TAE, TES, MOPS, MES, phosphate buffer, citric acid, CHES, acetic acid, borate, etc. In some embodiments, a reagent comprises additives to promote solubility (e.g., urea, guanidine HCL, detergents, sugars etc.), stability, etc. of the peptides within the reagent. In some embodiments, a reagent comprises one of more solvents, such at acetonitrile, methanol, ethanol, hexane, chloroform, etc.

In some embodiments, the methods and reagents find use in quality control of any suitable analytic instruments (e.g., LC, HPLC, MS (e.g., Atmospheric Pressure Ion sources (API), Electrospray or nebulization assisted Electrospray (ES), Atmospheric Pressure Chemical Ionization (APCI), Matrix Assisted Laser Desorption Ionization (MALDI), etc.), LC-MS, LC-MS/MS etc.). In some embodiments, a reagent is selected, prepared, and/or configured for use with a specific type of instrument (e.g., LC, MS, LC-MS, or LC-MS/MS). In other embodiments, a reagent is specifically selected, prepared, and/or configured to be used with a variety of instruments. In some embodiments, a reagent is selected, prepared, and/or configured for performing specific quality control assessments (e.g., calibration, performance evaluation, system suitability, etc.).

In some embodiments, the data generated by analysis (e.g., LC, MS, etc.) of a reagent is analyzed manually by a user or a trained specialist. In other embodiments, software and/or a package of software is provided to perform automated characterization of the reagent analysis. In some embodiments, software analyzes and reports on LC parameters (e.g., peak separation, peak efficiency, peak height, peak width, peak shape, retention time, etc.) and/or MS parameters (e.g., mass accuracy, mass resolution, sensitivity, dynamic range and sampling and/or isolation efficiency). In some embodiments, software correlates peaks in an LC and/or MS analysis to peptides and/or peptide isomers in the reagent. In some embodiments, software draws conclusions about instrument performance based on instrumental analysis. In some embodiments, software compares reagent analyses performed at different time points (e.g., separated by minutes, hours, days, weeks, years, etc.) to monitor changes in instrument performance. In some embodiments, software calibrates instrument data display/output to offset changes in instrument performance over time. In some embodiments, the software utilizes identifiers for the individual peptides, peptide mix, and/or reagent being analyzed in data analysis. In such embodiments, the software correlates the data with the known physical characteristics of the individual peptides, peptide mix, and/or reagent. In certain embodiments, software analysis automatically makes determinations regarding instrument sensitivity and/or dynamic range. In some embodiments, the software will report on instrument performance history. In other embodiments, the software report on a comparison of performance between multiple instruments. In some embodiments, the software generates a performance score.

In some embodiments, kits are provided that comprise a peptide reagent and one or more of additional reagents, software, container(s), instructions, additional peptide reagent, etc. In some embodiments, suitable aliquots of a peptide reagent are provided in a tube or other suitable container. In some embodiments, a kit provides multiple quality control reagents, useful for performing multiple quality control procedures.

EXPERIMENTAL

Example 1

Preparation and Evaluation of Heavy Labeled Peptides

Experiments were conducted during development of embodiments of the present invention to develop and evaluate heavy labeled peptides that: are a good indicator of the ability of a column to bind and elute both hydrophilic and hydrophobic peptides, provide a measure of an instrument's sensitivity and dynamic range, and provide information on additional instrument parameters discussed herein.

Selection and Design of Peptides:

Peptides were derived from a collection of tryptic peptides originating from a human plasma sample that had been depleted of albumin and IgG. Analysis of the data facilitated the identification of approximately 8300 unique peptides. Peptides containing W, M, C, P, N, Q, and N-terminal E/D were removed from consideration due to stability concerns. Peptides containing histidine were not considered since they added additional charge to the peptides. Furthermore, only fully tryptic peptides were considered (those with internal lysines and arginines were removed from consideration). Further, only peptides that had the ability to incorporate up to at least 7 stable isotopically-labeled residues and could allow for a mass difference of at least 4 Daltons per variant were selected for further consideration.

Peptides were grouped into 6 bins based on retention times. A set of approximately 20 peptides per bin were then selected based on signal intensity. These peptides were synthesized in crude form, combined into 10 mixtures and analyzed independently on an LTQ-Orbitrap Velos Mass Spectrometer. Properties such as retention time, peak shape, signal intensity, most abundant charge state and the ability to produce high quality $MS^2$ data were then used in the selection of the last round of peptides. The last set of peptides consisted of 28 peptides (spread across the 6 bins) which were then used to arrive at the final set of peptides. In selecting the final set of peptides (whose concentration was predetermined using amino-acid analysis (AAA)), a final set of peptides was required to be detectable down to 0.1 fmol (starting from 1 pmole; 5 orders of magnitude). In some embodiments, final peptide candidates were required to be detectable over a very large dynamic range, sensitive limit of detection and good chromatographic peak shape. In some embodiments, each of the final peptide candidates was required to contain at least 7 amino acids that could facilitate the isotopic incorporation of stable, heavy isotopically-labeled amino acids that would provide variants with mass differences of at least 4 Daltons between each other such that all 5 peptide isomers within the sample could be clearly resolved so that an accurate measurement of the peak area of all isotopes within the peptide envelope could be measured and integrated.

Figure 16:
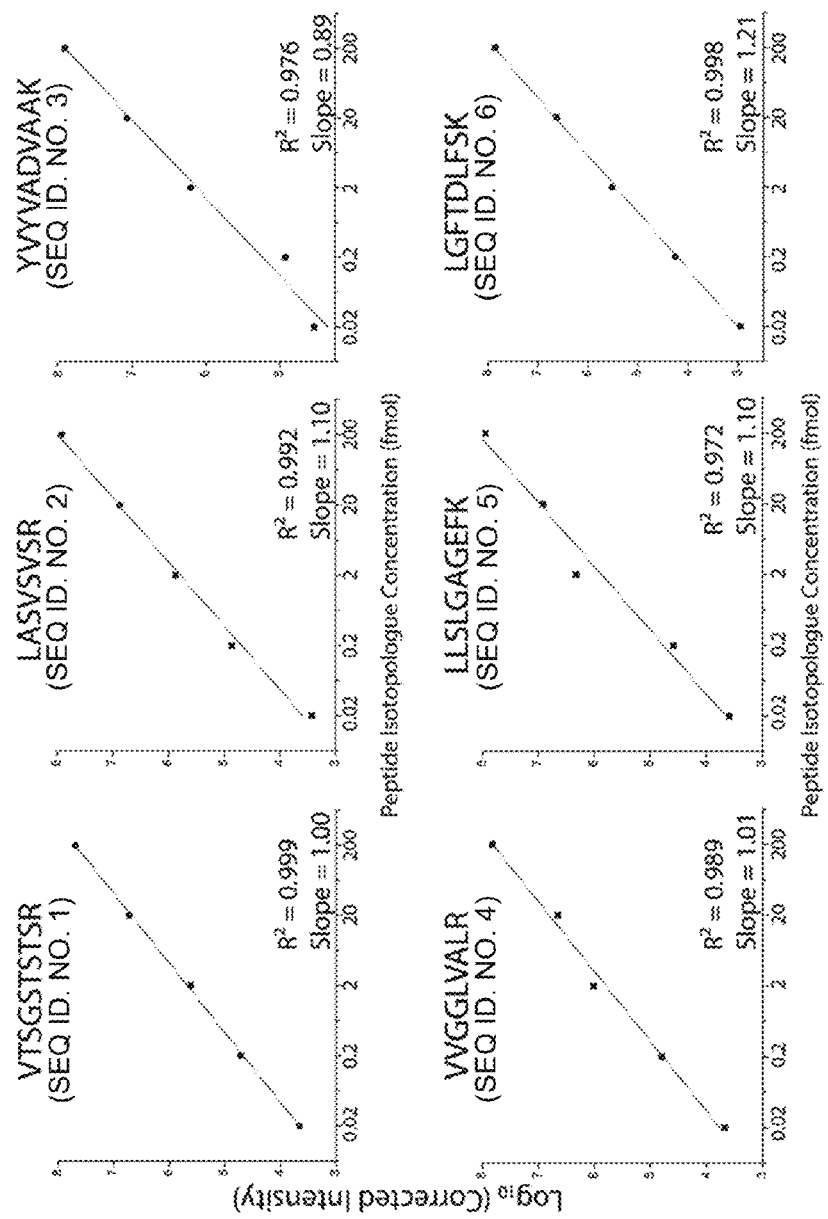
FIG. 16 shows MS analysis of a reagent comprising five distinct-mass versions of each of six distinct-sequence peptides, in which each successively lighter version of each peptide is present at 10-fold concentration excess over the immediately lighter version.
Figure 17:
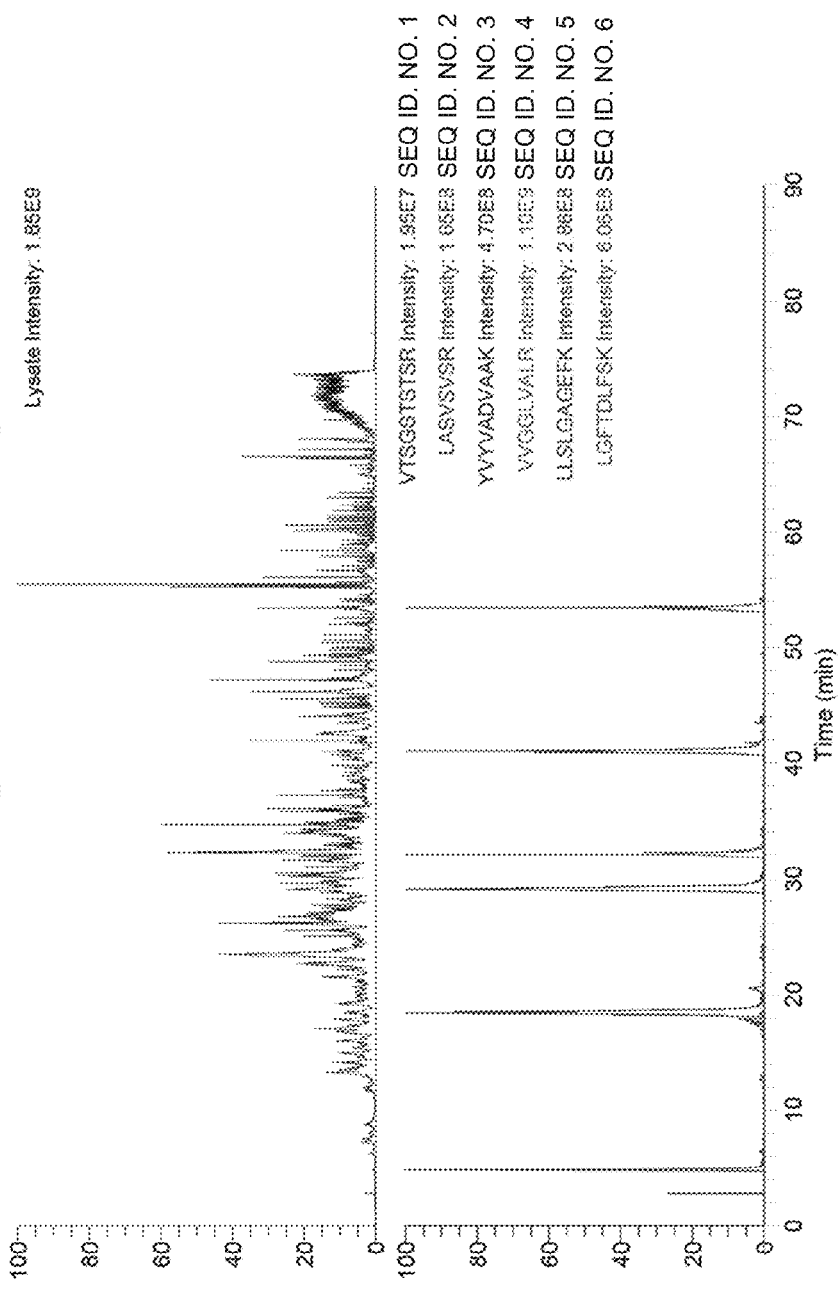
FIG. 17 shows chromatographic detection of all peptides when spiked into a complex background of a yeast tryptic digest.

Experimental Methods:

Peptides were synthesized by New England Peptide using, where appropriate, peptides with stable, heavy isotopes (uniform $^{13}C/^{15}N$ labeling). The following amino acids were required for various peptides (see Table 4 below) with the number in parenthesis indicating the mass shift in Daltons: (V, +6), (T, +5), (S, +4), (L,+7), (A,+4), (K,+8), (R,+10), (F, +10). Following purification, the peptides were subjected to amino-acid analysis so the precise molar amount could be determined. A mixture of 30 peptides was prepared in 2 formats (See Table 5). Both formats contained the same set of 6 peptides with each peptide having a set of 5 isomeric variants (30 peptides total). The isomers were identical in sequence, but contained different heavy labeled amino acids so that they would be distinguished by differing masses. These masses were used to generate standard curves so as to determine instrument sensitivity and dynamic range. The specific details of the variants and mixtures are given in Table 5 below. Format number 1 consisted of peptides in which each set of identical sequence (but variable with regard to isomer and mass) would differ by a 10-fold difference (either increasing or decreasing amount) of peptide amount. Format 2 was similar to format 1 with the exception that the decrease from one mass to the next is a 3-fold decrease. FIG. 16 provides an example of what the 6 standard curves would look like after correction for peak intensities. Additionally, all peptides contained at least one labeled amino acid to prevent isobaric interference when analyzing samples from human plasma, etc.

TABLE 4

Preparation of Peptide Stock Solutions

| Peptide Number | Code | Peptide Sequence | MW |
|---|---|---|---|
| 1 | SEQ ID NO. 1 | VTSGSTSTSR | 1016.532675 |
| 2 | SEQ ID NO. 1 | VTSGSTSTSR | 1007.515175 |
| 3 | SEQ ID NO. 1 | VTSGSTSTSR | 1002.504675 |
| 4 | SEQ ID NO. 1 | VTSGSTSTSR | 997.494275 |
| 5 | SEQ ID NO. 1 | VTSGSTSTSR | 991.480375 |
| 6 | SEQ ID NO. 2 | LASVSVSR | 854.532475 |
| 7 | SEQ ID NO. 2 | LASVSVSR | 846.518275 |
| 8 | SEQ ID NO. 2 | LASVSVSR | 839.501075 |
| 9 | SEQ ID NO. 2 | LASVSVSR | 833.487275 |
| 10 | SEQ ID NO. 2 | LASVSVSR | 827.473475 |
| 11 | SEQ ID NO. 3 | YVYVADVAAK | 1131.644975 |
| 12 | SEQ ID NO. 3 | YVYVADVAAK | 1123.630775 |
| 13 | SEQ ID NO. 3 | YVYVADVAAK | 1117.616975 |
| 14 | SEQ ID NO. 3 | YVYVADVAAK | 1111.603175 |
| 15 | SEQ ID NO. 3 | YVYVADVAAK | 1105.589375 |
| 16 | SEQ ID NO. 4 | VVGGLVALR | 917.631375 |
| 17 | SEQ ID NO. 4 | VVGGLVALR | 910.614275 |
| 18 | SEQ ID NO. 4 | VVGGLVALR | 904.600375 |
| 19 | SEQ ID NO. 4 | VVGGLVALR | 898.586575 |
| 20 | SEQ ID NO. 4 | VVGGLVALR | 892.572775 |
| 21 | SEQ ID NO. 5 | LLSLGAGEFK | 1072.673175 |
| 22 | SEQ ID NO. 5 | LLSLGAGEFK | 1062.645975 |
| 23 | SEQ ID NO. 5 | LLSLGAGEFK | 1055.628775 |
| 24 | SEQ ID NO. 5 | LLSLGAGEFK | 1048.611575 |
| 25 | SEQ ID NO. 5 | LLSLGAGEFK | 1041.594475 |
| 26 | SEQ ID NO. 6 | LGFTDLFSK | 1068.641075 |
| 27 | SEQ ID NO. 6 | LGFTDLFSK | 1058.613775 |
| 28 | SEQ ID NO. 6 | LGFTDLFSK | 1048.586575 |
| 29 | SEQ ID NO. 6 | LGFTDLFSK | 1041.569375 |
| 30 | SEQ ID NO. 6 | LGFTDLFSK | 1034.552275 |

Bold residues indicate uniform $^{13}C/^{15}N$ labeling.

TABLE 5

Peptide mixture formats

| SEQ ID NO: | Peptide Sequence | [Peptide] (µM) | Fold Decrease from closest mass variant | Format |
|---|---|---|---|---|
| 2 | LASVSVSR | 10.00 | NA | 1 |
| 3 | YVYVADVAAK | 1.000 | 10x less | 1 |
| 3 | YVYVADVAAK | 0.100 | 10x less | 1 |

TABLE 5-continued

Peptide mixture formats

| SEQ ID NO: | Peptide Sequence | [Peptide] (μM) | Fold Decrease from closest mass variant | Format |
|---|---|---|---|---|
| 3 | YVYVADVAAK | 0.010 | 10x less | 1 |
| 3 | YVYVADVAAK | 0.001 | 10x less | 1 |
| 3 | YVYVADVAAK | 10.00 | NA | 1 |
| 4 | VVGGLVALR | 1.000 | 10x less | 1 |
| 4 | VVGGLVALR | 0.100 | 10x less | 1 |
| 4 | VVGGLVALR | 0.010 | 10x less | 1 |
| 4 | VVGGLVALR | 0.001 | 10x less | 1 |
| 4 | VVGGLVALR | 10.00 | NA | 1 |
| 5 | LLSLGAGEFK | 1.000 | 10x less | 1 |
| 5 | LLSLGAGEFK | 0.100 | 10x less | 1 |
| 5 | LLSLGAGEFK | 0.010 | 10x less | 1 |
| 5 | LLSLGAGEFK | 0.001 | 10x less | 1 |
| 5 | LLSLGAGEFK | 10.00 | NA | 1 |
| 6 | LGFTDLFSK | 1.000 | 10x less | 1 |
| 6 | LGFTDLFSK | 0.100 | 10x less | 1 |
| 6 | LGFTDLFSK | 0.010 | 10x less | 1 |
| 6 | LGFTDLFSK | 0.001 | 10x less | 1 |
| 6 | LGFTDLFSK | 10.00 | NA | 1 |
| 1 | VTSGSTSTSR | 1.000 | 10x less | 1 |
| 1 | VTSGSTSTSR | 0.100 | 10x less | 1 |
| 1 | VTSGSTSTSR | 0.010 | 10x less | 1 |
| 1 | VTSGSTSTSR | 0.001 | 10x less | 1 |
| 1 | VTSGSTSTSR | 10.00 | NA | 1 |
| 2 | LASVSVSR | 1.000 | 10x less | 1 |
| 2 | LASVSVSR | 0.100 | 10x less | 1 |
| 2 | LASVSVSR | 0.010 | 10x less | 1 |
| 2 | LASVSVSR | 0.001 | 10x less | 1 |
| 2 | LASVSVSR | 10.0 | NA | 2 |
| 3 | YVYVADVAAK | 3.30 | 3x less | 2 |
| 3 | YVYVADVAAK | 1.10 | 3x less | 2 |
| 3 | YVYVADVAAK | 0.34 | 3x less | 2 |
| 3 | YVYVADVAAK | 0.12 | 3x less | 2 |
| 3 | YVYVADVAAK | 10.0 | NA | 2 |
| 4 | VVGGLVALR | 3.30 | 3x less | 2 |
| 4 | VVGGLVALR | 1.10 | 3x less | 2 |
| 4 | VVGGLVALR | 0.34 | 3x less | 2 |
| 4 | VVGGLVALR | 0.12 | 3x less | 2 |
| 4 | VVGGLVALR | 10.0 | NA | 2 |

TABLE 5-continued

Peptide mixture formats

| SEQ ID NO: | Peptide Sequence | [Peptide] (μM) | Fold Decrease from closest mass variant | Format |
|---|---|---|---|---|
| 5 | LLSLGAGEFK | 3.30 | 3x less | 2 |
| 5 | LLSLGAGEFK | 1.10 | 3x less | 2 |
| 5 | LLSLGAGEFK | 0.34 | 3x less | 2 |
| 5 | LLSLGAGEFK | 0.12 | 3x less | 2 |
| 5 | LLSLGAGEFK | 10.0 | NA | 2 |
| 6 | LGFTDLFSK | 3.30 | 3x less | 2 |
| 6 | LGFTDLFSK | 1.10 | 3x less | 2 |
| 6 | LGFTDLFSK | 0.34 | 3x less | 2 |
| 6 | LGFTDLFSK | 0.12 | 3x less | 2 |
| 6 | LGFTDLFSK | 10.0 | NA | 2 |
| 2 | LASVSVSR | 3.30 | 3x less | 2 |
| 3 | YVYVADVAAK | 1.10 | 3x less | 2 |
| 3 | YVYVADVAAK | 0.34 | 3x less | 2 |
| 3 | YVYVADVAAK | 0.12 | 3x less | 2 |
| 3 | YVYVADVAAK | 10.0 | NA | 2 |
| 3 | YVYVADVAAK | 3.30 | 3x less | 2 |
| 4 | VVGGLVALR | 1.10 | 3x less | 2 |
| 4 | VVGGLVALR | 0.34 | 3x less | 2 |
| 4 | VVGGLVALR | 0.12 | 3x less | 2 |

Un-bolded residues indicate uniform $^{13}C/^{15}N$ labeling

The peptides (30 total) were mixed into a solution and 200 fmol of this solution was loaded onto a $C_{18}$ capillary LC Column (75 μm×15 cm). The LC gradient, typically 1 hour, was ramped from 2.5% buffer B (Buffer A–0.1% formic acid in water and Buffer B–acetonitrile/0.1% FA) until 40% B. Mass spectra were collected, in real time, immediately after following LC. All mass spectra were collected on either a Thermo LTQ-Orbitrap Velos or Q Exactive mass spectrometer operating at MS resolutions of 60,000 with calibrated mass accuracies below 3 ppm. Samples were acquired with a mass range of 350-1200 m/z such that multiply charged (+2/+3) peptides would trigger MS/MS scans.

The peptides of Table 4 were analyzed by LC and MS, both in the formats described in Table 5 and in other combinations (e.g., isotopologue mixes (e.g., the lightest version of each peptide sequence, second lightest of each peptide sequence . . . heaviest version of each peptide sequence)), to assess, for example peptide characteristics and analysis procedures.

The effect of loading time on the binding of the peptides to the LC column was examined (See FIG. 5). It was determined that shorter loading times (e.g., 2.5 min) were preferential for the binding of all of the peptides, in particular the most hydrophilic sequence (VTSGSTSTSR (SEQ ID NO: 1)).

Figure 6:
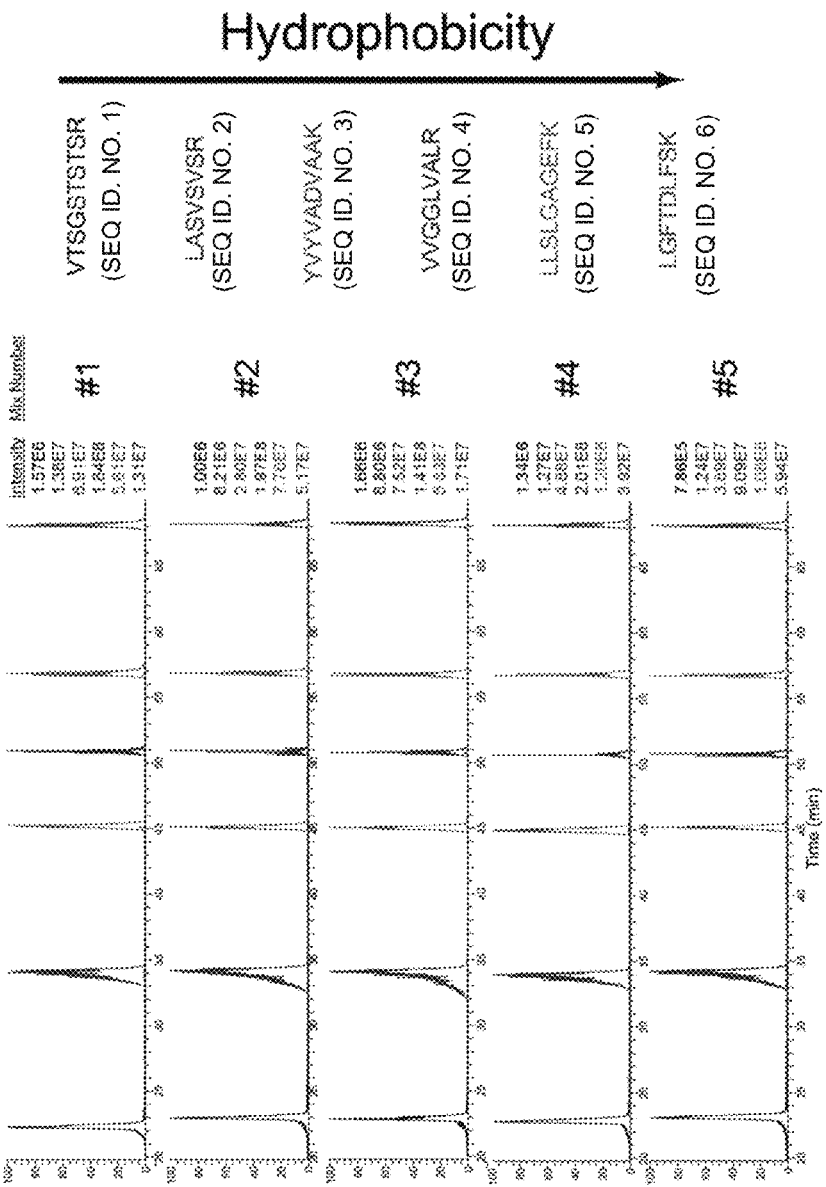
FIG. 6 shows LC analysis of 5 isotopologue mixes of peptides, demonstrating that each isomeric peptide, regardless of mass, co-elutes from the column.

FIG. 6 depicts an LC analysis of sotopologue mixes (e.g., the lightest version of each peptide sequence, second lightest of each peptide sequence . . . heaviest version of each peptide sequence) of the peptides of Table 4. Mix #1 consisted of the "lightest" peptide only from each set, and each mix was prepared with a progressively heavier variant. Thus, mix #5 contained the "heaviest" form of each peptide. The data indicate that although the peptides contain different types of stable, heavy labeled amino acids, they are chemically identical (See FIG. 6).

Figure 7:
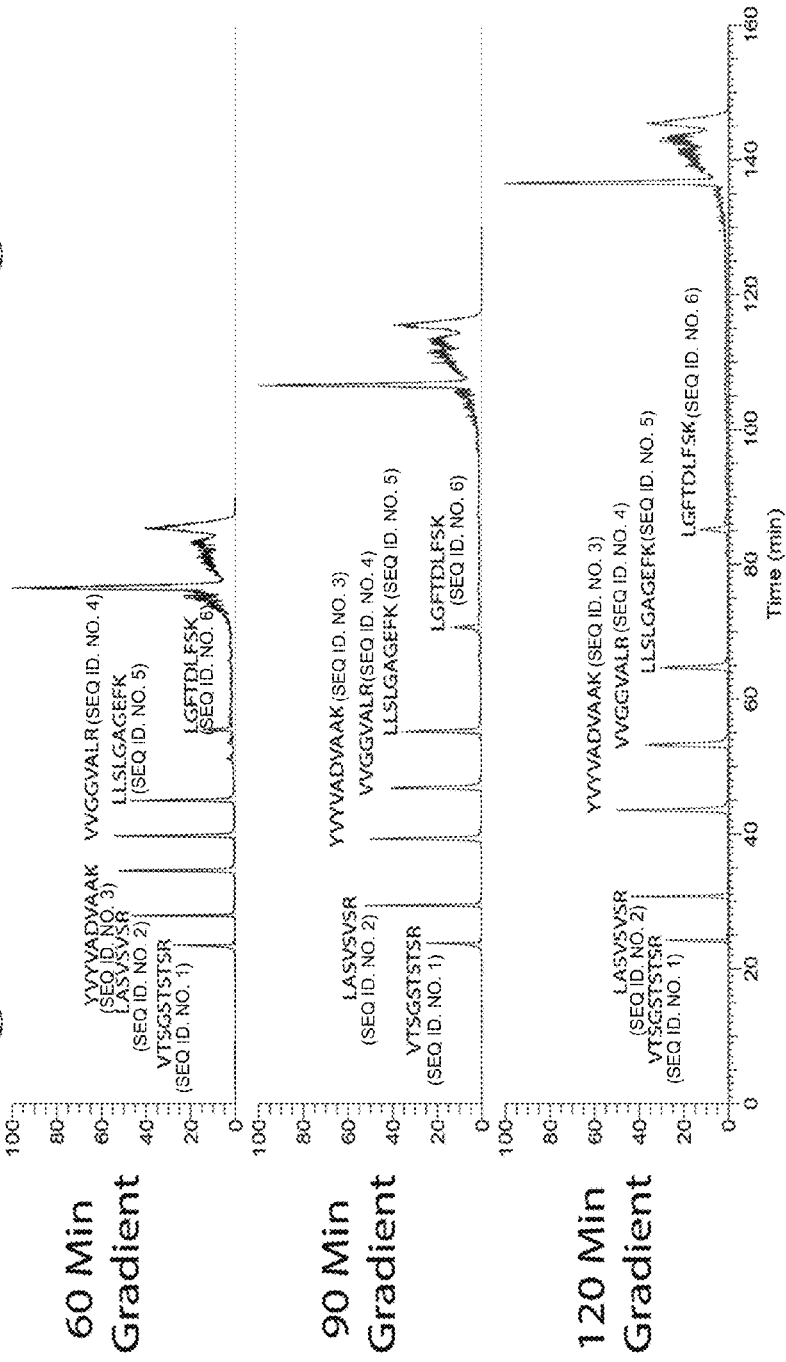
FIG. 7 shows LC analysis of peptide mix using different chromatographic gradients (Buffer A=0.1% formic acid in water and Buffer B=0.1% formic acid in acetonitrile). Regardless of the gradient, separation and peak shape is retained in all cases.

A mix of 6 peptide sequences (all equimolar) was subjected to chromatographic gradients (Buffer A=0.1% Formic acid in water and Buffer B=0.1% formic acid in acetonitrile; (60 min gradient: 25% B/60 minutes; 90 minute gradient: 25% B/90 minutes; 120 minutes: 25% B/120 minutes). Regardless of the gradient, adequate separation and sharp peak shape was observed for all six peptide sequences (See FIG. 7).

Figure 8:
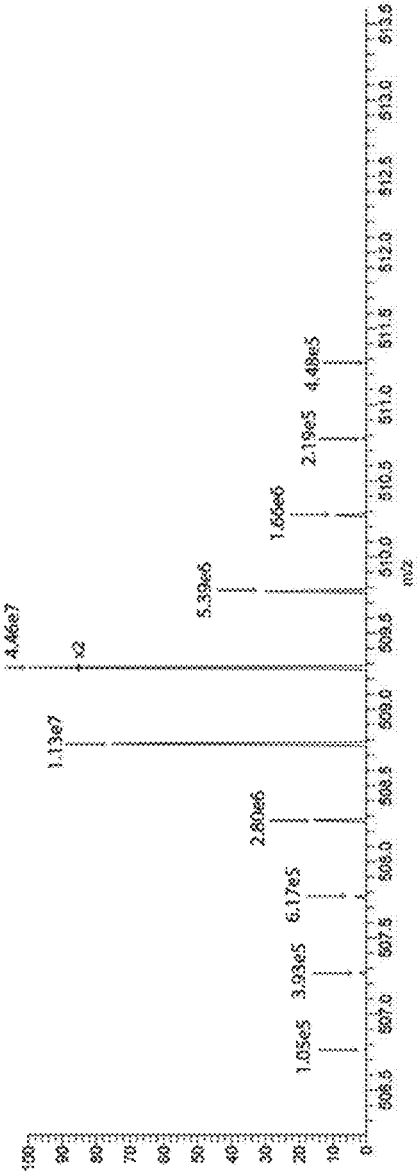
FIG. 8 shows a graph used to calculate correction factors used for peptide quantification. Correction factors are required to normalize all peak intensities to correct for distribution of naturally occurring, heavy isotopes. The correction factor represents the ratio of the monoisotopic m/z intensity to the total isotopic distribution intensity and is used to derive the correct intensity of the ion when all isotopes cannot be fully detected.

In order to quantify the amount of a given peptide in a sample mixture (e.g., in order to achieve reliable linear correlations), a correction factor was calculated for each of the peptide variants since the isotopic spread (envelope) is different depending on the level of isotope incorporation (See FIG. 8). To calculate the corrected intensities, the intensities of the visible isotopes are summed, and the sum of the intensities of each is then divided by the intensity of the tallest peak. This value then gives a correction factor for each peptide variant and thus allows for the normalization of the peak intensity (See FIG. 8).

Figure 9:
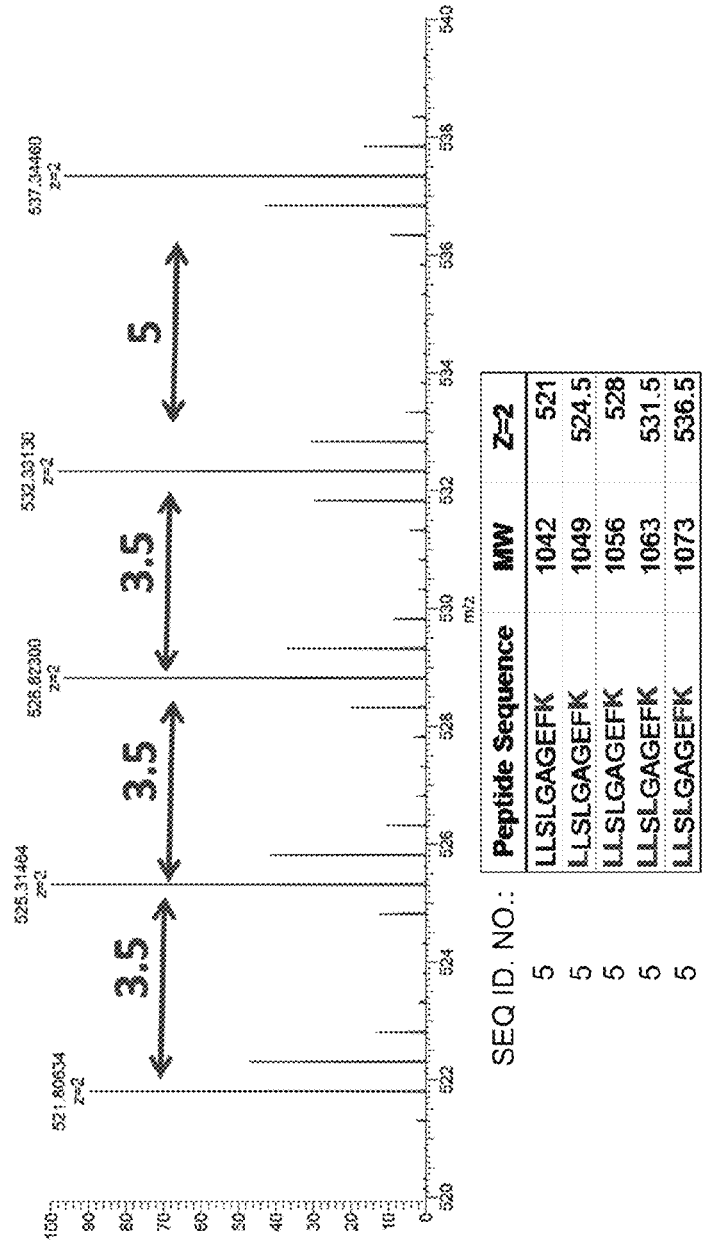
FIG. 9 shows a representative mass spectrum of five distinct mass versions of a single peptide sequence. These masses (which are the doubly charged peptides) are easily resolved on unit resolution instruments. This is particularly clear in this example, albeit at high-resolution.
Figure 10:
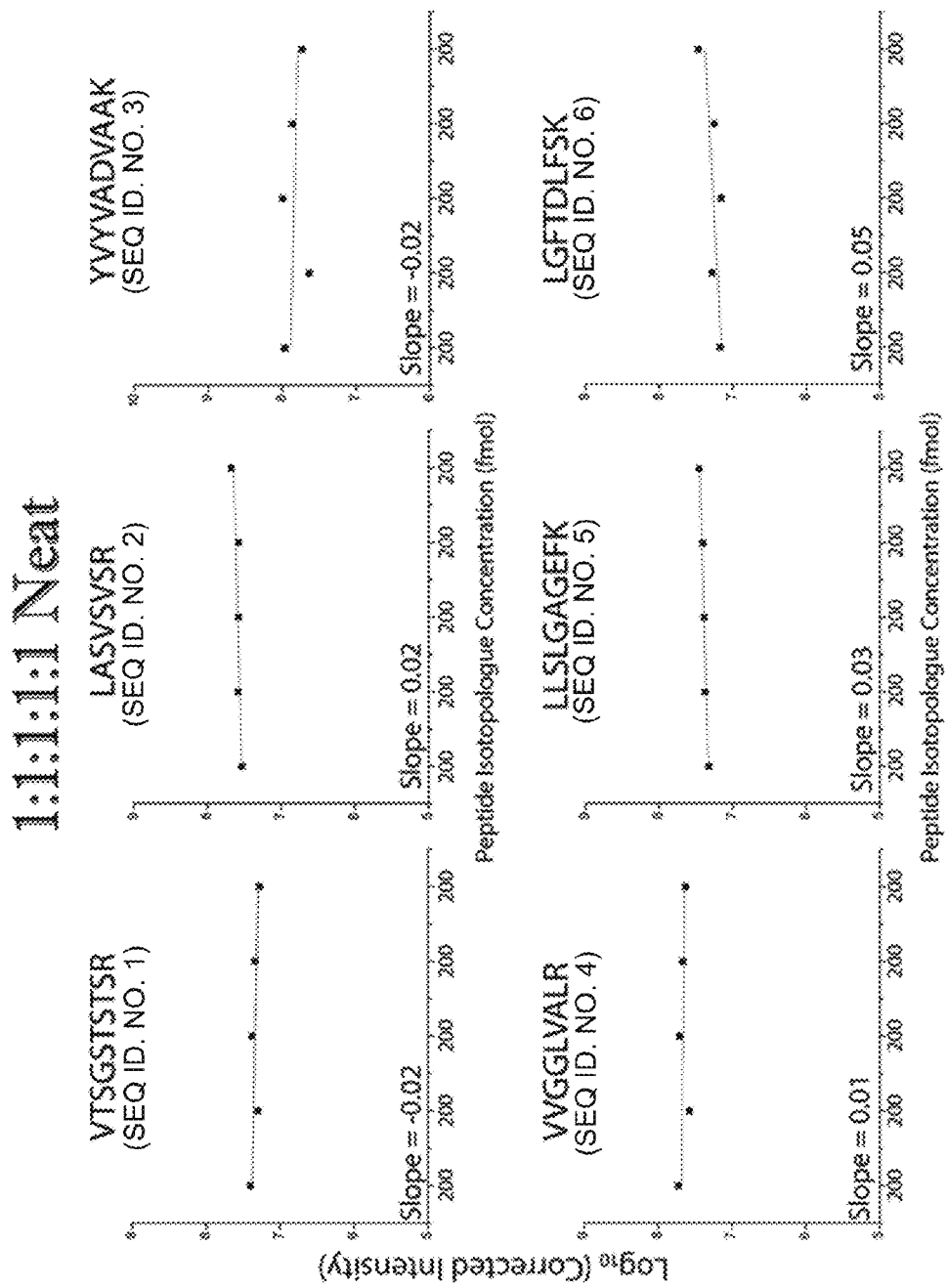
FIG. 10 shows the results of MS analysis of a peptide reagent comprising five distinct-mass versions of each of six distinct-sequence peptides.

Mass spectra were taken of the various peptide sequences (See, e.g., FIG. 9). In this example, each different mass version of the peptide sequence was supplied at equal concentration. As a result, approximately equal intensities were observed, with mass separations of at least? Daltons (note that we are observing the doubly charged peptides and thus have m/z spacings of 3.5 Daltons, respectively). Next, all 30 of the peptides of Table 4 were analyzed by MS in an equimolar mixture. The molar amounts of each of the peptides (200 fmole) are plotted versus the log of the corrected signal intensity (FIG. 10). The peptides, when mixed equally, give equal intensities as predicted.

Figure 11:
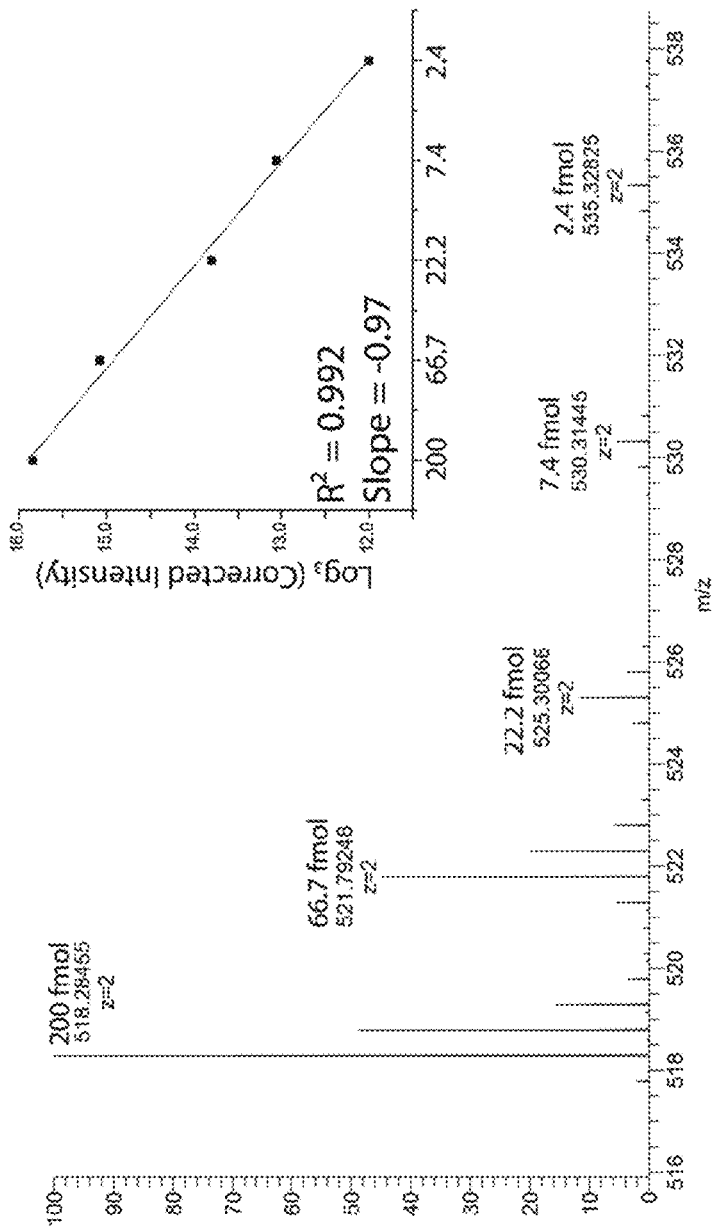
FIG. 11 shows linear analysis of the mass spectrum of a reagent comprising five distinct mass versions of a single peptide sequence.
Figure 12:
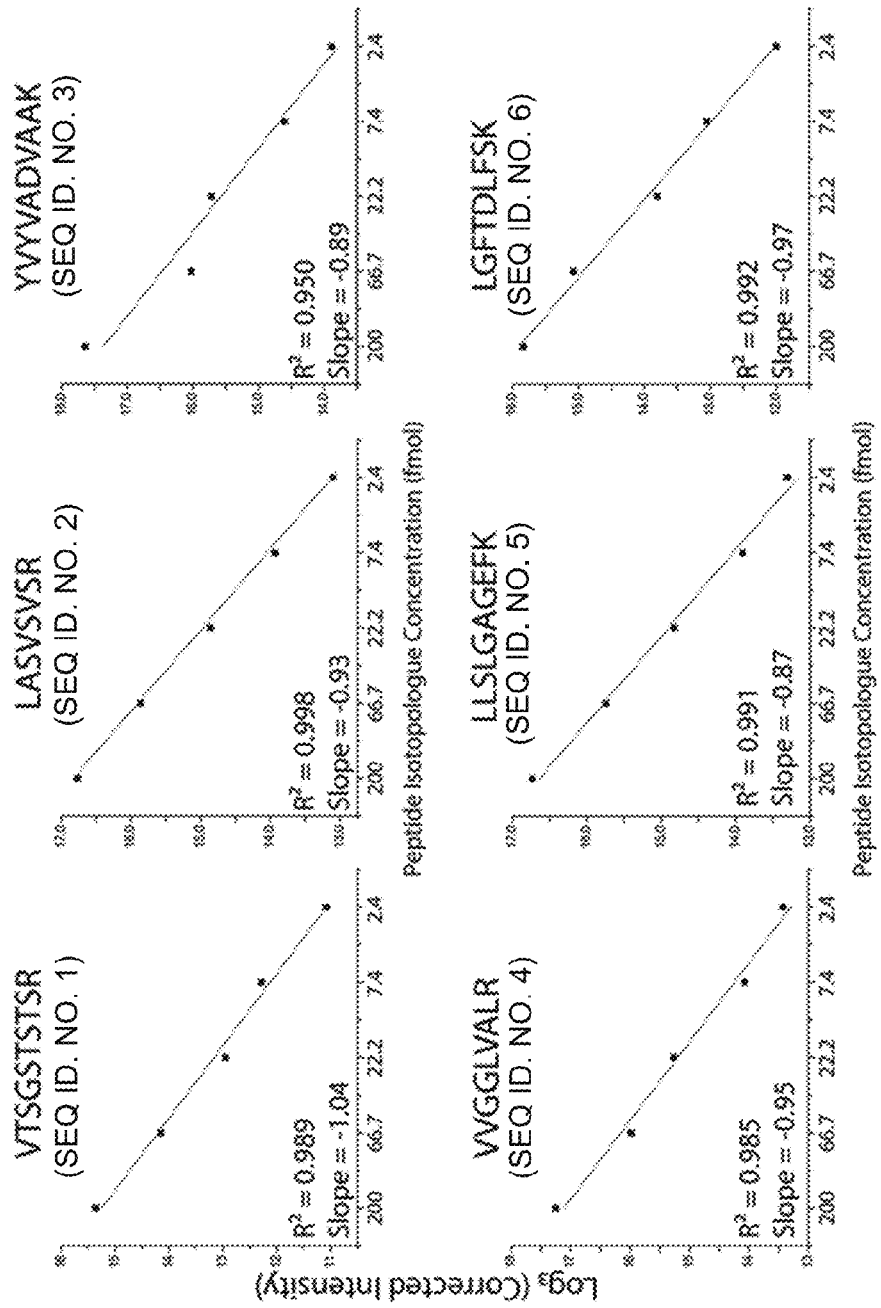
FIG. 12 shows linear analysis of the mass spectrum of a reagent comprising five distinct-mass versions of each of six distinct-sequence peptides.
Figure 13:
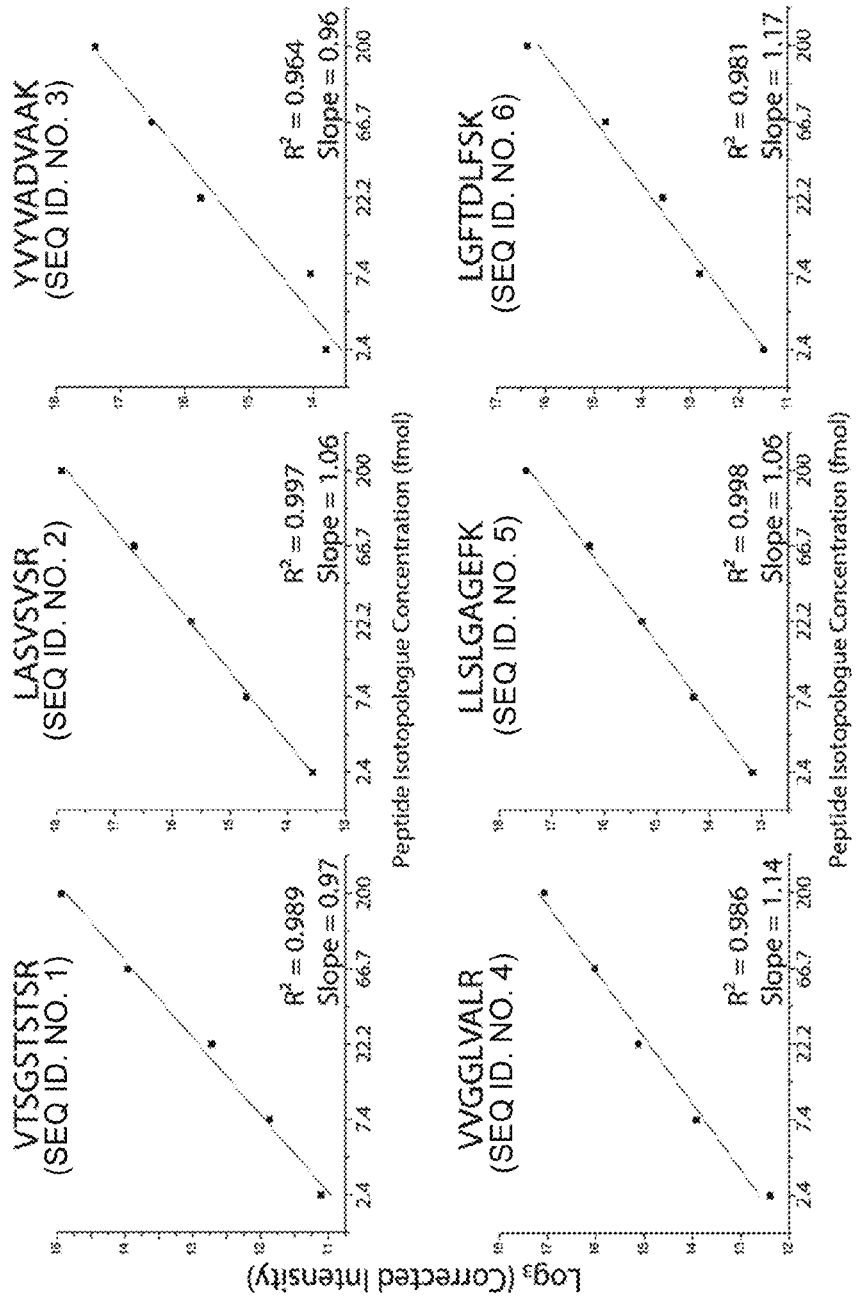
FIG. 13 shows linear analysis of the mass spectrum of a reagent comprising five distinct-mass versions of each of six distinct-sequence peptides (reversed concentrations from FIG. 12).
Figure 14:
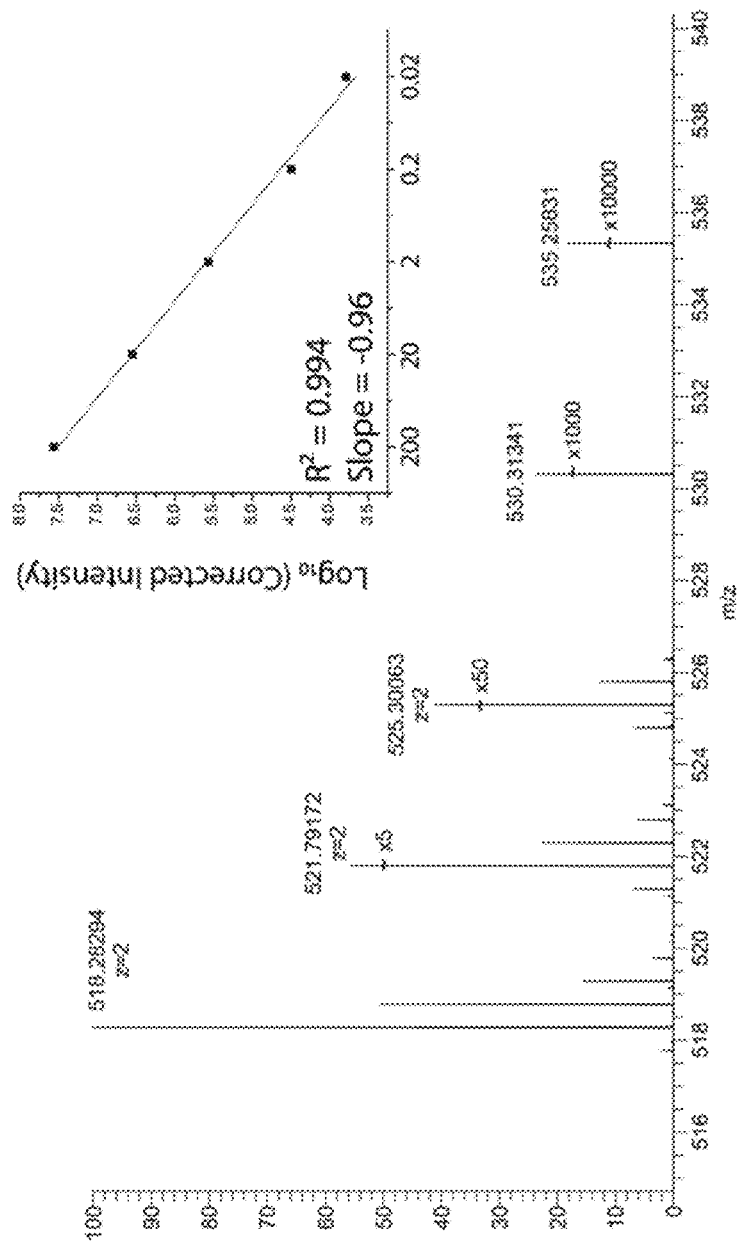
FIG. 14 shows MS analysis of five distinct mass versions of a single peptide sequence, in which each successively heavier version is present at 10-fold concentration excess over the immediately lighter version.
Figure 15:
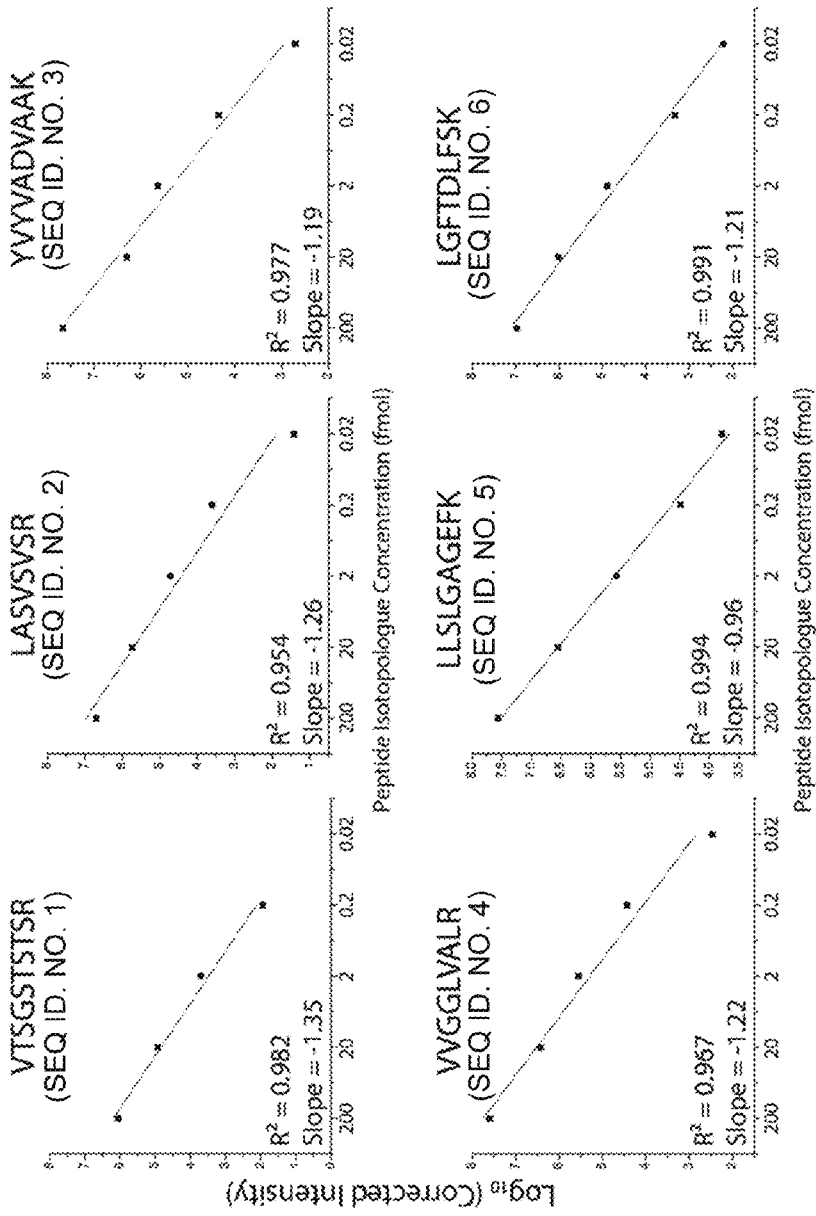
FIG. 15 shows MS analysis of a reagent comprising five distinct-mass versions of each of six distinct-sequence peptides, in which each successively heavier version of each peptide is present at 10-fold concentration excess over the immediately lighter version.

In addition to the analysis of equimolar samples, format 2 from Table 5, in which different-mass version of each peptide sequence are present at successive 3-fold concentration differences, were analyzed by MS (See, e.g., FIG. 11). Such analysis demonstrates a linear relationship between the five mass variants prepared with a 3-fold drop in log base 3 of intensity as a function of increasing mass. Similar linear relationships were observed for all the sequences tested (See, e.g., FIGS. 12 and 13). Whether the most abundant peptide was the heaviest (FIG. 13) or lightest (FIG. 12) peptide of the given sequence, the same relationship was observed. The proportional relationship was observed upon MS analysis of mixtures of format 1 from Table 5, containing different-mass version of each peptide sequence present at successive 10-fold concentration differences (See FIGS. 14-16).

Figure 18:
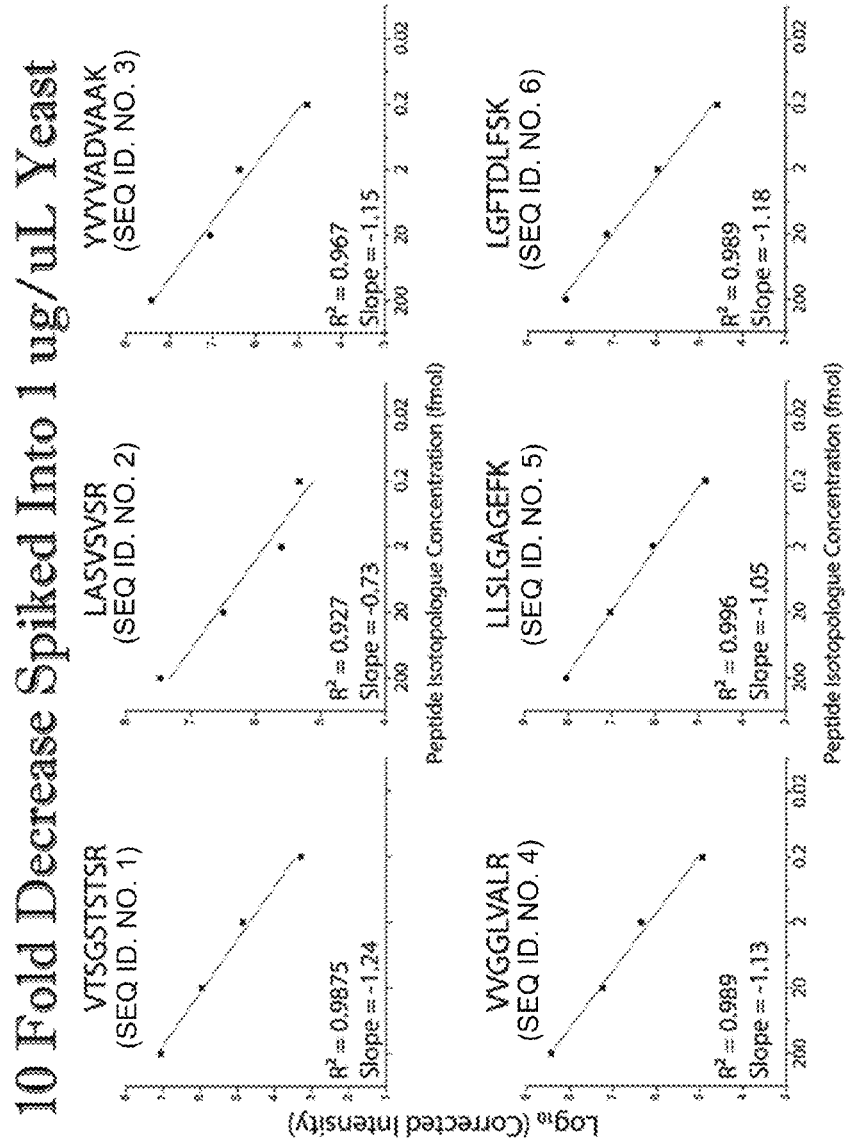
FIG. 18 shows the lowest detectable peptide quantity (LDPQ) analysis of a reagent comprising five distinct-mass versions of each of six distinct-sequence peptides in a yeast tryptic digest background (starting concentration 2 fmol). Note that, with this mixture, all of the peptides are detectable down to 200 amol, despite being present in a highly complex mixture.
Figure 19:
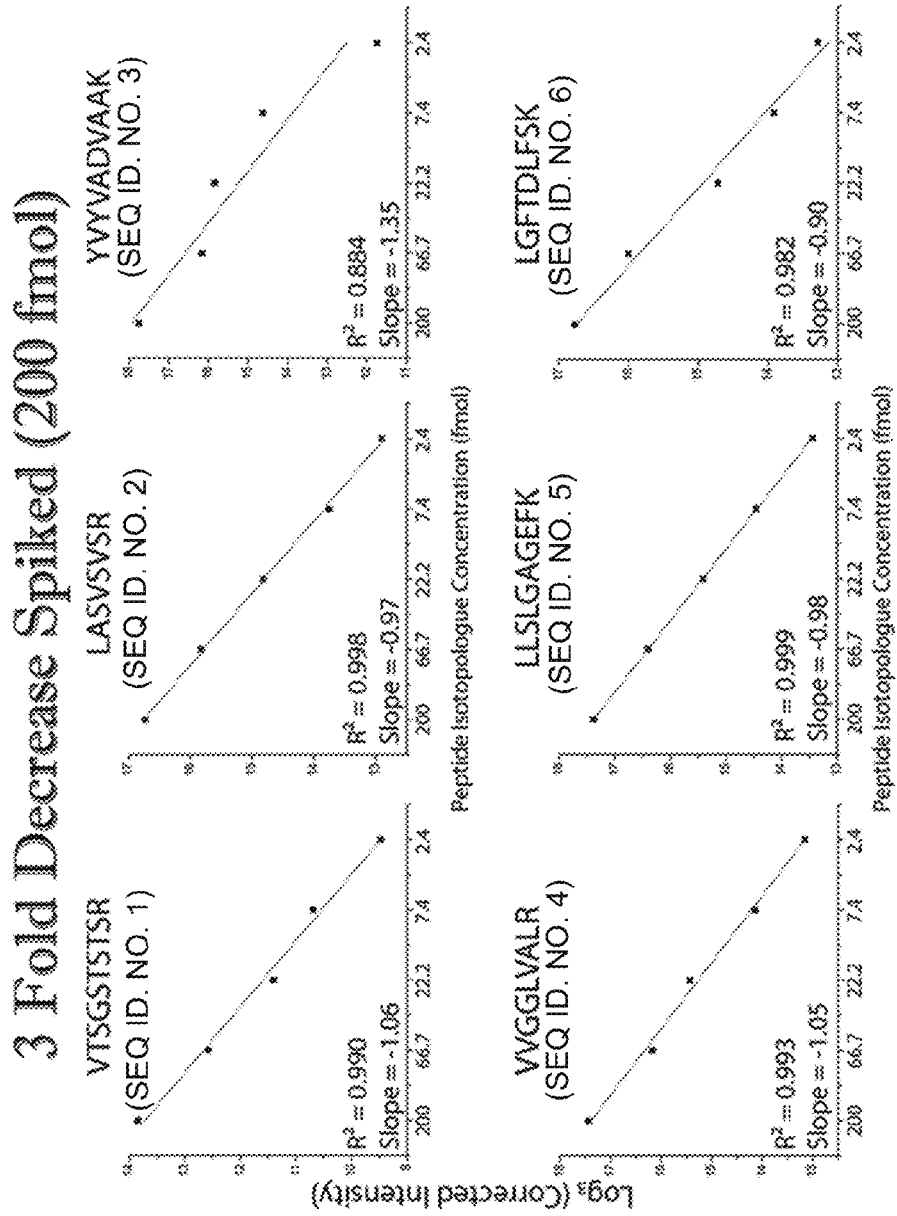
FIG. 19 shows limit of quantification (LOQ) analysis of a reagent comprising five distinct-mass versions of each of six distinct-sequence peptides in a yeast background (starting concentration of 200 fmol).
Figure 20:
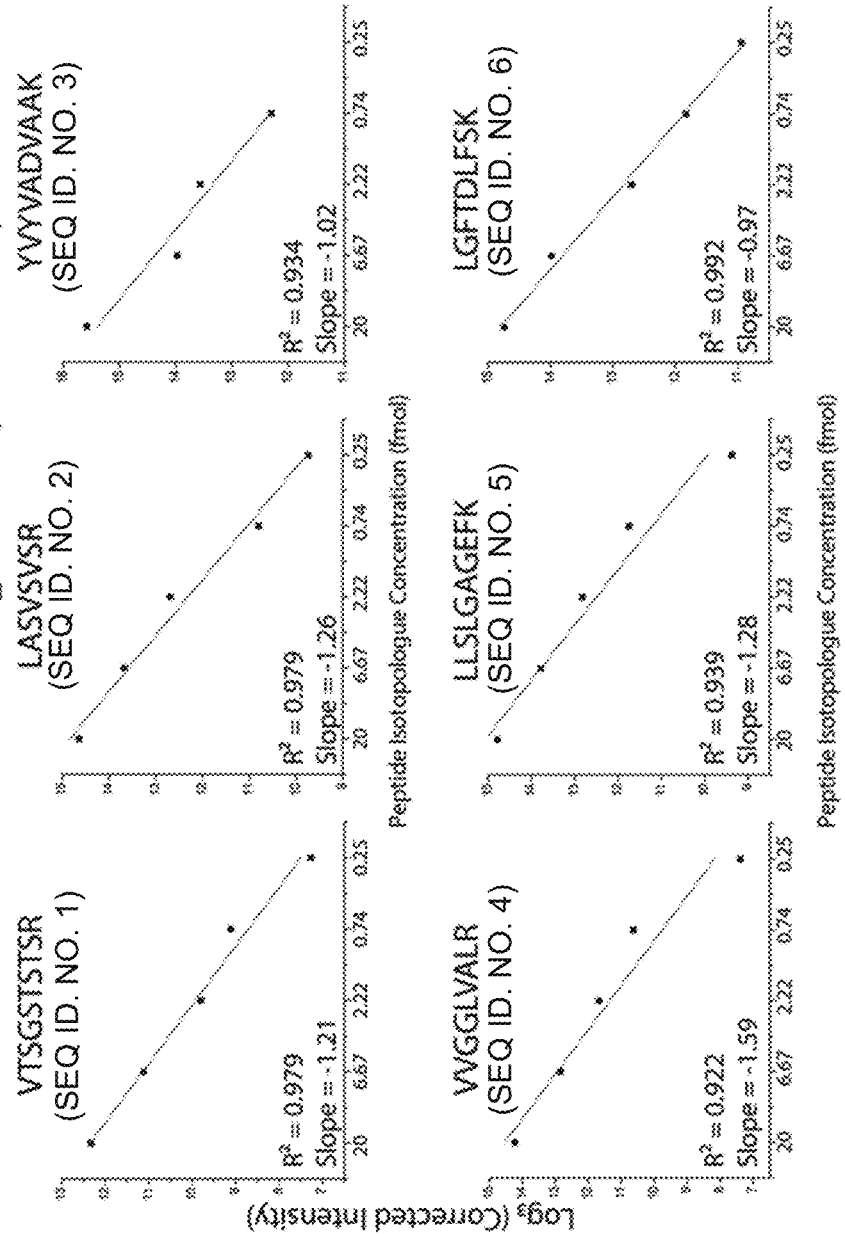
FIG. 20 shows limit of quantification (LOQ) analysis of a reagent comprising five distinct-mass versions of each of six distinct-sequence peptides in a yeast background, following a second dilution (starting concentration of 20 fmol).
Figure 21:
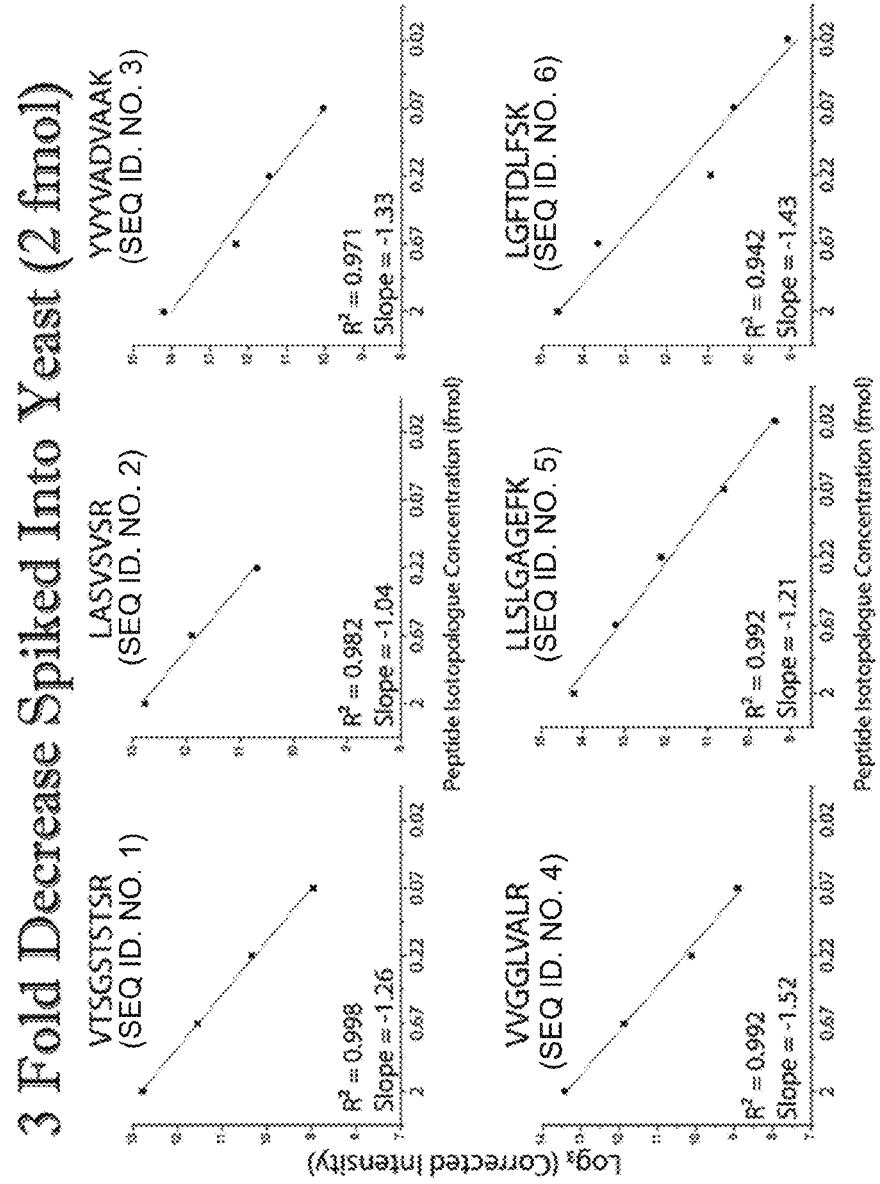
FIG. 21 shows limit of quantification (LOQ) analysis of a reagent comprising five distinct-mass versions of each of six distinct-sequence peptides in a yeast background, following a second dilution (starting concentration of 2 fmol).

Detection of all peptides in a format 2 mixture was possible when the peptides were spiked into a complex background of 1 µg/1 µL yeast tryptic digest (See FIG. 18). An upper bound of quantitation analysis of the peptide set in yeast background revealed that detection could not extend below 200 amol (See FIG. 19), but indicated that a dilution of the spiked sample would facilitate such detection. When the starting concentration is 200 fmol, the detection limit goes down to 2.4 fmol (See FIG. 19). When the starting concentration is 20 fmol, the detection limit goes down to 250 amol (See FIG. 20). When the starting concentration is 2 fmol, the detection limit goes down to 20 amol (See FIG. 21). Thus a method for determining absolute instrument sensitivity (and possibly LOD and LOQ) has been established.

The invention claimed is:

1. A peptide mixture comprising three or more distinct-mass versions of each of two or more distinct-sequence peptides, wherein two or more of the distinct-sequence peptides are selected from SEQ ID NOS: 1-6, and wherein two or more of the distinct-mass versions of each distinct-sequence peptide comprises one or more amino acids with above natural-abundance levels of one or more heavy isotopes.

2. The peptide mixture of claim 1, wherein all of the distinct-mass versions of any of the distinct-sequence peptides are present at distinct concentrations.

3. The peptide mixture of claim 2, wherein the distinct-mass versions of any of the distinct-sequence peptides are present at concentrations ranging from at least as low as 10 nM to at least as high at 1 μM.

4. The peptide mixture of claim 3, wherein the distinct-mass versions of any of the distinct-sequence peptides are present at concentrations ranging from 1 nM (femtomoles per microliter) to 10 µM.

5. The peptide mixture of claim 1, wherein the distinct-sequence peptides are separable by liquid chromatography based on their different hydrophobicities.

6. The peptide mixture of claim 1, wherein the distinct-sequence peptides are separable by liquid chromatography based on their different charge, size, or hydrophilicity.

7. The peptide mixture of claim 1, comprising 3-20 distinct-sequence peptides.

8. The peptide mixture of claim 7, comprising 5-10 distinct-sequence peptides.

9. The peptide mixture of claim 1, wherein the distinct-mass versions of any of the distinct-sequence peptides are differentiable by mass spectrometry.

10. The peptide mixture of claim 1, wherein the distinct-mass versions of any of the distinct-sequence peptides are the result of different combinations of stable heavy isotope-labeled amino acids.

11. The peptide mixture of claim 10, wherein each of the distinct-mass versions of any of the distinct-sequence peptides comprises a different number of uniformly stable isotope-labeled amino acids.

12. The peptide mixture of claim 1, comprising 3-20 distinct-mass versions of each of the distinct-sequence peptides.

13. The peptide mixture of claim 12, comprising 5-10 distinct-mass versions of each of the distinct-sequence peptides.

14. The peptide mixture of claim 1, comprising three or more distinct mass versions of peptides of each of SEQ ID NOS: 1-6.

15. The peptide mixture of claim 1, comprising six distinct-sequence peptides comprising SEQ ID NOS: 1-6.

16. The peptide mixture of claim 15, comprising peptides selected from: V*T*S*GST*ST*SR* (SEQ ID NO: 1), V*T*SGST*ST*SR* (SEQ ID NO: 1), V*T*SGSTSTSR* (SEQ ID NO: 1), V*TSGSTSTSR* (SEQ ID NO: 1), VTSGSTSTSR* (SEQ ID NO: 1), L*A*SV*SV*SR* (SEQ ID NO: 2), L*ASV*SV*SR* (SEQ ID NO: 2), LASV*SV*SR* (SEQ ID NO: 2), LASVSV*SR* (SEQ ID NO: 2), LASVSVSR* (SEQ ID NO: 2), YV*YV*ADV*A*A*K* (SEQ ID NO: 3), YV*YV*ADV*AAK* (SEQ ID NO: 3), YVYV*ADV*AAK* (SEQ ID NO: 3), YVYVADV*AAK* (SEQ ID NO: 3), YVYVADVAAK* (SEQ ID NO: 3), V*V*GGL*V*ALR* (SEQ ID NO: 4), V*V*GGLV*ALR* (SEQ ID NO: 4), V*V*GGLVALR* (SEQ ID NO: 4), V*VGGLVALR* (SEQ ID NO: 4), VVGGLVALR* (SEQ ID NO: 4), L*L*SL*GAGEF*K* (SEQ ID NO: 5), L*L*SL*GAGEFK* (SEQ ID NO: 5), L*L*SLGAGEFK* (SEQ ID NO: 5), L*LSLGAGEFK* (SEQ ID NO: 5), LLSLGAGEFK* (SEQ ID NO: 5), L*GF*TDL*F*SK* (SEQ ID NO: 6), L*GFTDL*F*SK* (SEQ ID NO: 6), L*GFTDL*FSK* (SEQ ID NO: 6), L*GFTDLFSK* (SEQ ID NO: 6), and LGFTDLFSK* (SEQ ID NO: 6) wherein * following a residue indicates above natural-abundance levels of one or more heavy isotopes.

17. The peptide mixture of claim 1, comprising peptides selected from: V*T*S*GST*ST*SR* (SEQ ID NO: 1), V*T*SGST*ST*SR* (SEQ ID NO: 1), V*T*SGSTSTSR* (SEQ ID NO: 1), V*TSGSTSTSR* (SEQ ID NO: 1), VTSGSTSTSR* (SEQ ID NO: 1), L*A*SV*SV*SR* (SEQ ID NO: 2), L*ASV*SV*SR* (SEQ ID NO: 2), LASV*SV*SR* (SEQ ID NO: 2), LASVSV*SR* (SEQ ID NO: 2), LASVSVSR* (SEQ ID NO: 2), YV*YV*ADV*A*A*K* (SEQ ID NO: 3), YV*YV*ADV*AAK* (SEQ ID NO: 3), YVYV*ADV*AAK* (SEQ ID NO: 3), YVYVADV*AAK* (SEQ ID NO: 3), YVYVADVAAK* (SEQ ID NO: 3), V*V*GGL*V*ALR* (SEQ ID NO: 4), V*V*GGLV*ALR* (SEQ ID NO: 4), V*V*GGLVALR* (SEQ ID NO: 4), V*VGGLVALR* (SEQ ID NO: 4), VVGGLVALR* (SEQ ID NO: 4), L*L*SL*GAGEF*K* (SEQ ID NO: 5), L*L*SL*GAGEFK* (SEQ ID NO: 5), L*L*SLGAGEFK* (SEQ ID NO: 5), L*LSLGAGEFK* (SEQ ID NO: 5), LLSLGAGEFK* (SEQ ID NO: 5), L*GF*TDL*F*SK* (SEQ ID NO: 6), L*GFTDL*F*SK* (SEQ ID NO: 6), L*GFTDL*FSK* (SEQ ID NO: 6), L*GFTDLFSK* (SEQ ID NO: 6), and LGFTDLFSK* (SEQ ID NO: 6) wherein * following a residue indicates above natural-abundance levels of one or more heavy isotopes.

18. The peptide mixture of claim 17, comprising peptides comprising: V*T*S*GST*ST*SR* (SEQ ID NO: 1), V*T*SGST*ST*SR* (SEQ ID NO: 1), V*T*SGSTSTSR* (SEQ ID NO: 1), V*TSGSTSTSR* (SEQ ID NO: 1), VTSGSTSTSR* (SEQ ID NO: 1), L*A*SV*SV*SR* (SEQ ID NO: 2), L*ASV*SV*SR* (SEQ ID NO: 2), LASV*SV*SR* (SEQ ID NO: 2), LASVSV*SR* (SEQ ID NO: 2), LASVSVSR* (SEQ ID NO: 2), YV*YV*ADV*A*A*K* (SEQ ID NO: 3), YV*YV*ADV*AAK* (SEQ ID NO: 3), YVYV*ADV*AAK* (SEQ ID NO: 3), YVYVADV*AAK* (SEQ ID NO: 3), YVYVADVAAK* (SEQ ID NO: 3), V*V*GGL*V*ALR* (SEQ ID NO: 4), V*V*GGLV*ALR* (SEQ ID NO: 4), V*V*GGLVALR* (SEQ ID NO: 4), V*VGGLVALR* (SEQ ID NO: 4), VVGGLVALR* (SEQ ID NO: 4), L*L*SL*GAGEF*K* (SEQ ID NO: 5), L*L*SL*GAGEFK* (SEQ ID NO: 5), L*L*SLGAGEFK* (SEQ ID NO: 5), L*LSLGAGEFK* (SEQ ID NO: 5), LLSLGAGEFK* (SEQ ID NO: 5), L*GF*TDL*F*SK* (SEQ ID NO: 6), L*GFTDL*F*SK* (SEQ ID NO: 6), L*GFTDL*FSK* (SEQ ID NO: 6), L*GFTDLFSK* (SEQ ID NO: 6), and LGFTDLFSK* (SEQ ID NO: 6) wherein * following a residue indicates above natural-abundance levels of one or more heavy isotopes.

* * * * *

SEQUENCE LISTING

```
<160> NUMBER OF SEQ ID NOS: 9

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Val Thr Ser Gly Ser Thr Ser Thr Ser Arg
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Leu Ala Ser Val Ser Val Ser Arg
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Tyr Val Tyr Val Ala Asp Val Ala Ala Lys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4
```

```
Val Val Gly Gly Leu Val Ala Leu Arg
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic

<400> SEQUENCE: 5

Leu Leu Ser Leu Gly Ala Gly Glu Phe Lys
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Leu Gly Phe Thr Asp Leu Phe Ser Lys
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

Leu Leu Ser Leu Gly Ala Leu Glu Phe Lys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic

<400> SEQUENCE: 8

Leu Ser Ser Leu Gly Ala Leu Glu Phe Lys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Ala Ala Pro Gly Glu Asp Ser Arg Lys Tyr
1               5                   10
```